US006774225B2

(12) United States Patent
Yong

(10) Patent No.: US 6,774,225 B2
(45) Date of Patent: *Aug. 10, 2004

(54) ANTIGENIZED ANTIBODY VACCINE FOR FOOT-AND-MOUTH DISEASE

(75) Inventor: Xie Yong, Kowloon (HK)

(73) Assignee: Hong Kong University of Science & Technology (HK)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/291,299

(22) Filed: Apr. 15, 1999

(65) Prior Publication Data

US 2002/0076405 A1 Jun. 20, 2002

(51) Int. Cl.[7] ............................................... C07H 21/04
(52) U.S. Cl. ................ 536/23.4; 536/23.53; 536/23.72; 514/44
(58) Field of Search .......................... 514/44; 536/23.4, 536/23.53, 23.72

(56) References Cited

U.S. PATENT DOCUMENTS

| | | | | |
|---|---|---|---|---|
| 4,743,554 A | * | 5/1988 | Boothroyd et al. | 435/253 |
| 5,700,680 A | * | 12/1997 | Newton et al. | 435/240.2 |
| 5,824,316 A | * | 10/1998 | Grubman et al. | 424/216.1 |

OTHER PUBLICATIONS

Bona et al., Immunogenicity of Microbial Peptides Grafted in Self Immunoglobulin Molecules, Cellular and Molecular Biology, 40 (Suppl. I), 21–30, 1994.
Francis, Peptide Vaccines: New Approaches to Immunopotentiation Vaccines: New–Generation Immunological Adjuvants, New York, 1995, 135–141.
Tam, Synthetic Peptide Vaccine Design: Synthesis and Properties of a High–Density Multiple Antigenic Peptide System, Proc. Natl. Acad. Sci. USA, vol. 85, pp 5409–5413, Aug. 1988.
Francis, Enhanced Immunogenicity of Recombinant and Synthetic Peptide Vaccines, Vaccines, Edited by G. Gregoriadis et al., New York, 1991, pp 13–23.
Broekhuijsen et al., Synthesis of Fusion Proteins with Multiple Copies of an Antigenic Determinant of Foot–and–Mouth Disease Virus, Medical Biological Laboratory TNO, 1986, pp 189–197.
Winther et al., Bacterially Expressed Antigenic Peptide from Foot–and–Mouth Disease Virus Capsid Elicits Variable Immunologic Respones in Animals, Journal of Immunology, 1986, vol. 136 No. 5, pp 1835–1840.
Krzych et al., Repertoires of T Cells Directed Against a Large Protein Antigen, β Galactosidase, Journal of Immunology, vol. 126 No. 4, 1982, pp 1529–1534.
Manca et al., Constraints in T–B Cooperation Related to Epitope Topology on E. Coli β–Galactosidase, Journal of Immunology, 1985, 15, pp. 345–350.
Broekhuijsen et al., Fusion Proteins with Multiple Copies of the Major Antigenic Determinant of Foot–and–Mouth Disease Virus Protect Both the Natural Host and Laboratory Animals, J Gen Virol, 1987, 68, 3137–3143.

* cited by examiner

Primary Examiner—Donna C. Wortman
(74) Attorney, Agent, or Firm—Baker & McKenzie

(57) ABSTRACT

A vaccine for treatment of foot-and-mouth disease of swine is provided. This vaccine is an antigenized antibody vaccine created from the grafting of peptide epitopes derived from FMDV into swine antibody CDR loops. FMDV peptide epitopes are cloned by PCR from VP1 gene of FMDV. The overlapping PCR method is used to insert the FMDV peptide epitopes into the CDR regions of swine immnuoglobulin heavy and light chains genes. The resulting antigenized antibody genes were cloned into mammalian expression vector. The plasmids are transfected into CHO or myeloma cells. The stable transfectant cell line was selected for high yield of the desired protein vaccine.

12 Claims, 17 Drawing Sheets

MEFRLNWVVL FALLQGVQGE EKLVESGGGL VQPGGSLKLS CVGSGFTFSS
TYIHWVRQAP GKGLEWLAGL YSSTTPTYYS DSVKGRFDIS REDAQNTAYL
QMNGLKTEDTARYYCGKRHK
QEIVAPVKQK LWGPGVEVVV SSAPKTAPSVYP LAPCGRDVSG
PNVALGCLAS SYFPEPVTVT WNSGALTSGV HTFPSVLQPSGLYSLSSMVT
VPASSLSSKS YTCNVNHPAT TTKVDKRVGI HQPQTCPICP GCEVAGPSVF
IFPPKPKDTL MISQTPEVTC VVVDVSKEHA EVQFSWYVDG VEVHTAETRP
KEEQFNSTYRVVSVLPIQHQ DWLKGKEFKC KVNNVDLPAP ITRTISKAIG
QSREPQVYTL PPPAEELSRSKVTLTCLVIG FYPPDIHVEW KSNGQPEPEN
TYRTTPPQQD VDGTFFLYSK LAVDKARWDHGDKFECAVMH
EALHNHYTQK SISKTQGK

Figure 3

```
  1 ATGGAGTTTC GGCTGAACTG GGTGGTCTTG TTTGCTCTCT
TACAAGGTGT CCAGGGTGAG
 61 GAGAAGCTGG TGGAGTCTGG AGGAGGCCTGGTGCAGCCTG
GGGGGTCTCT GAAACTCTCC
121 TGTGTCGGCT CTGGATTCAC CTTCAGTAGT ACCTATATTC
ACTGGGTCCG CCAGGCTCCA
181 GGGAAGGGAC TGGAGTGGCT GGCAGGTCTC TACAGTAGTA
CTACGCCGAC CTACTACTCA
241 GACTCTGTGA AGGGCCGGTT CGACATCTCC AGAGAGGACG
CCCAGAACAC GGCCTATCTA
301 CAAATGAACG GCCTGAAAAC CGAAGACACG GCCCGCTACT
ACTGTGGAAA GCGTCACAAA
361 CAGGAAATCG TAGCTCCAGT AAAACAGAAG TTGTGGGGCC
CAGGCGTTGA AGTCGTCGTG
421 TCCTCAGCCC CCAAGACGGC CCCATCGGTC TACCCTCTGG
CCCCCTGCGG CAGGGACACG
481 TCTGGCCCTA ACGTGGCCTT GGGCTGCCTG GCCTCAAGCT
ACTTCCCCGA GCCAGTGACC
541 ATGACCTGGA ACTCGGGCGC CCTGACCAGT GGCGTGCACA
CCTTCCCATC CGTCCTGCAG
601 CCGTCAGGGC TCTACTCCCT CAGCAGCATG GTGACCGTGC
CGGCCAGCAG CCTGTCCAGC
661 AAGAGCTACA CCTGCAATGT CAACCACCCG GCCACCACCA
CCAAGGTGGA CAAGCGTGTT
721 GGAATACACC AGCCGCAAAC ATGTCCCATA TGCCCAGGCT
GTGAAGTGGC CGGGCCCTCG
781 GTCTTCATCT TCCCTCCAAA ACCCAAGGAC ACCCTCATGA
TCTCCCAGAC CCCCGAGGTC
841 ACGTGCGTGG TGGTGGACGT CAGCAAGGAG CACGCCGAGG
TCCAGTTCTC CTGGTACGTG
901 GACGGGGTAG AGGTGCACAC GGCCGAGACG AGACCAAAGG
AGGAGCAGTT CAACAGCACC
961 TACCGTGTGG TCAGCGTCCT GCCCATCCAG CACCAGGACT
GGCTGAAGGG GAAGGAGTTC
1021 AAGTGCAAGG TCAACAACGT AGACCTCCCA GCCCCCATCA
CGAGGACCAT CTCCAAGGCT
1081 ATAGGGCAGA GCCGGGAGCC GCAGGTGTAC ACCCTGCCCC
CACCCGCCGA GGAGCTGTCC
1141 AGGAGCAAAG TCACGCTAAC CTGCCTGGTC ATTGGCTTCT
ACCCACCTGA CATCCATGTT
1201 GAGTGGAAGA GCAACGGACA GCCGGAGCCA GAGAACACAT
ACCGCACCAC CCCGCCCCAG
1261 CAGGACGTGG ACGGGACCTT CTTCCTGTAC AGCAAACTCG
CGGTGGACAA GGCAAGATGG
1321 GACCATGGAG ACAAATTTGA GTGTGCGGTG ATGCACGAGG
CTCTGCACAA CCACTACACC
1381 CAGAAGTCCA TCTCCAAGAC TCAGGGTAAA TGAGCCACCC
GCTGCACCCC ACGTGCTCTC
1441 GGGTCCCGCG AGCTCGCCTG AGCCCAGCG CTGTGTACAT
ACGTCCCGGG CCAGCATGAA
1501 ATAAA
```

Figure 4

MEFRLNWVVL FALLQGVQGE EKLVESGGGL VQPGGSLKLS CVGSGFTFSS TYIHWVRQAP
GKGLEWLAGL YSSTTPTYYS DSVKGRFDIS REDAQNTAYL QMNGLKTEDT ARYYCGKVPN
LRGDLQVLAQ KVARTLPWGP GVEVVVSS APKTAPSVYP LAPCGRDVSG
PNVALGCLAS SYFPEPVTVT WNSGALTSGV HTFPSVLQPSGLYSLSSMVT
VPASSLSSKS YTCNVNHPAT TTKVDKRVGI HQPQTCPICP GCEVAGPSVF
IFPPKPKDTL MISQTPEVTC VVVDVSKEHA EVQFSWYVDG VEVHTAETRP
KEEQFNSTYR VVSVLPIQHQ DWLKGKEFKC KVNNVDLPAP ITRTISKAIG
QSREPQVYTL PPPAEELSRSKVTLTCLVIG FYPPDIHVEW KSNGQPEPEN
TYRTTPPQQD VDGTFFLYSK LAVDKARWDHGDKFECAVMH
EALHNHYTQK SISKTQGK

Figure 5

1 ATGGAGTTTC GGCTGAACTG GGTGGTCTTG TTTGCTCTCT
TACAAGGTGT CCAGGGTGAG
    61 GAGAAGCTGG TGGAGTCTGG AGGAGGCCTG GTGCAGCCTG
GGGGGTCTCT GAAACTCTCC
   121 TGTGTCGGCT CTGGATTCAC CTTCAGTAGT ACCTATATTC
ACTGGGTCCG CCAGGCTCCA
   181 GGGAAGGGAC TGGAGTGGCT GGCAGGTCTC TACAGTAGTA
CTACGCCGAC CTACTACTCA
   241 GACTCTGTGA AGGGCCGGTT CGACATCTCC AGAGAGGACG
CCCAGAACAC GGCCTATCTA
   301 CAAATGAACG GCCTGAAAAC CGAAGACACG GCCCGCTACT
ACTGTGGAAA GGTACCAAAC
   361 **CTGCGTGGTG ACCTGCAGGT ACTTGCTCAG AAAGTTGCTC
GTACTCTGCC** ATGGGGCCCA
   421 GGCGTTGAAG TCGTCGTGTC CTCAGCCCCC AAGACGGCCC
CATCGGTCTA CCCTCTGGCC
   481 CCCTGCGGCA GGGACACGTC TGGCCCTAAC GTGGCCTTGG
GCTGCCTGGC CTCAAGCTAC
   541 TTCCCCGAGC CAGTGACCAT GACCTGGAAC TCGGGCGCCC
TGACCAGTGG CGTGCACACC
   601 TTCCCATCCG TCCTGCAGCC GTCAGGGCTC TACTCCCTCA
GCAGCATGGT GACCGTGCCG
   661 GCCAGCAGCC TGTCCAGCAA GAGCTACACC TGCAATGTCA
ACCACCCGGC CACCACCACC
   721 AAGGTGGACA AGCGTGTTGG AATACACCAG CCGCAAACAT
GTCCCATATG CCCAGGCTGT
   781 GAAGTGGCCG GGCCCTCGGT CTTCATCTTC CCTCCAAAAC
CCAAGGACAC CCTCATGATC
   841 TCCCAGACCC CCGAGGTCAC GTGCGTGGTG GTGGACGTCA
GCAAGGAGCA CGCCGAGGTC
   901 CAGTTCTCCT GGTACGTGGA CGGGGTAGAG GTGCACACGG
CCGAGACGAG ACCAAAGGAG
   961 GAGCAGTTCA ACAGCACCTA CCGTGTGGTC AGCGTCCTGC
CCATCCAGCA CCAGGACTGG
  1021 CTGAAGGGGA AGGAGTTCAA GTGCAAGGTC AACAACGTAG
ACCTCCCAGC CCCCATCACG
  1081 AGGACCATCT CCAAGGCTAT AGGGCAGAGC CGGGAGCCGC
AGGTGTACAC CCTGCCCCCA
  1141 CCCGCCGAGG AGCTGTCCAG GAGCAAAGTC ACGCTAACCT
GCCTGGTCAT TGGCTTCTAC
  1201 CCACCTGACA TCCATGTTGA GTGGAAGAGC AACGGACAGC
CGGAGCCAGA GAACACATAC
  1261 CGCACCACCC CGCCCCAGCA GGACGTGGAC GGGACCTTCT
TCCTGTACAG CAAACTCGCG
  1321 GTGGACAAGG CAAGATGGGA CCATGGAGAC AAATTTGAGT
GTGCGGTGAT GCACGAGGCT
  1381 CTGCACAACC ACTACACCCA GAAGTCCATC TCCAAGACTC
AGGGTAAATG AGCCACCCGC
  1441 TGCACCCCAC GTGCTCTCGG GTCCCGCGAG CTCGCCTGAG
CCCCAGCGCT GTGTACATAC
  1501 GTCCCGGGCC AGCATGAAAT AAA

Figure 6

```
   1 GTACCAAACC TGCGTGGTGA CCTGCAGGTA CTTGCTCAGA
AAGTTGCTCG TACTCTGCCA
  61 CGTCACAAAC AGGAAATCGT AGCTCCAGTA AAACAGAAGT
TGGCCCCCAA GACGGCCCCA
 121 TCGGTCTACC CTCTGGCCCC CTGCGGCAGG GACGTGTCTG
GCCCTAACGT GGCCTTGGGC
 181 TGCCTGGCCT CAAGCTACTT CCCCGAGCCA GTGACCGTGA
CCTGGAACTC GGGCGCCCTG
 241 ACCAGTGGCG TGCACACCTT CCCATCCGTC CTGCAGCCGT
CAGGGCTCTA CTCCCTCAGC
 301 AGCATGGTGA CCGTGCCGGC CAGCAGCCTG TCCAGCAAGA
GCTACACCTG CAATGTCAAC
 361 CACCCGGCCA CCACCACCAA GGTGGACAAG CGTGTTGGAA
TCATCTTCCC GCAAACATGT
 421 CCCATATGCC CAGGCTGTGA AGTGGCCGGG CCCTCGGTCT
TCATCTIFCCC TCCAAAACCC
 481 AAGGACACCC TCATGATCTC CCAGACCCCC GAGGTCACGT
GCGTGGTGGT GGACGTCAGC
 541 AAGGAGCACG CCGAGGTCCA GTTCTCCTGG TACGTGGACG
GGGTAGAGGT GCACACGGCC
 601 GAGACGAGAC CAAAGGAGGA GCAGTTCAAC AGCACCTACC
GTGTGGTCAG CGTCCTGCCC
 661 ATCCAGCACC AGGACTGGCT GAAGGGGAAG GAGTTCAAGT
GCAAGGTCAA CAACGTAGAC
 721 CTCCCAGCCC CCATCACGAG GACCATCTCC AAGGCTATAG
GGCAGAGCCG GGAGCCGCAG
 781 GTGTACACCC TGCCCCCACC CGCCGAGGAG CTGTCCAGGA
GCAAAGTCAC GCTAACCTGC
 841 CTGGTCATTG GCTTCTACCC ACCTGACATC CATGTTGAGT
GGAAGAGCAA CGGACAGCCG
 901 GAGCCAGAGA ACACATACCG CACCACCCCG CCCCAGCAGG
ACGTGGACGG GACCTTCTTC
 961 CTGTACAGCA AACTCGCGGT GGACAAGGCA AGATGGGACC
ATGGAGACAA ATTTGAGTGT
1021 GCGGTGATGC ACGAGGCTCT GCACAACCAC TACACCCAGA
AGTCCATCTC CAAGACTCAG
1081 GGTAAATGA
```

Figure 7

```
ID F1-IGG            PRT; 363 AA.
SQ SEQUENCE 363 AA; 39864 MW; 748554 CN;

VPNLRGDLQV LAQKVARTLP RHKQEIVAPV KQKLAPKTAP
SVYPLAPCGR DVSGPNVALG
    CLASSYFPEP VTVTWNSGAL TSGVHTFPSV LQPSGLYSLS SMVTVPASSL
SSKSYTCNVN
    HPATTTKVDK RVGIHQPQTC PICPGCEVAG PSVFIFPPKP KDTLMISQTP
EVTCVVVDVS
    KEHAEVQFSW YVDGVEVHTA ETRPKEEQFN STYRVVSVLP
IQHQDWLKGK EFKCKVNNVD
    LPAPITRTIS KAIGQSREPQ VYTLPPPAEE LSRSKVTLTC LVIGFYPPDI
HVEWKSNGQP
    EPENTYRTTP PQQDVDGTFF LYSKLAVDKA RWDHGDKFEC
AVMHEALHNH YTQKSISKTQ
        GK*
```

Figure 8

PIGL1 sequence

DS QTVIQKPAISFSLGGTVTLT CAFSSGSLTG INYPSWFQRT
PGQPPQTVIY NTNNRPTGVP IRFSGAISGN KAALTITGAQ
AKDEADYFCA LYKSSAQITF
GGGTHLTVLG QPKAAPTVNL FPPSSEELGTNKATLVCLIS DFYPGAVTVT
WKAGGTTVTQ GVETTKPSKQ SNNKYAASSY LALSASDWKS SSGFTCQVTH
EGTIVEKTVT PSECA

PIGL2 Sequence

DSQTVIQEPAMSVSPGGTV TLTCAFTSGSVTTSNHPGWY QQTPGQPPRL
VIYRTNNRPT GVPSRFSGAI
SGNKAALSITGAQANDEADYFCTLWKDNTYFFGGGTRLTVLGQPKAAPM
V NLFPPSSEEL GTNKATLVCL ISDFYPGAVTVTWKAGGTTV TQGVETTKPS
KQSNNKYAAS S
YLALSASDW KSSSGFTCQV THEGTIVEKTVTPSECA

PIGL3 Sequence

DSQTVIQEP AMSVSPGGTV TVTCAFSSGS VTSSDYPSWF QQTPGQPPRT
VIYRTNKPPD
WVPGLSGAMSGNKASLTITGAQAEDEADYFCALEEKSRYQVFGGGTHLT
VLGQPKAAPTV NFFPPSSEEL GTNKATLVCL ISDFYPGAVT VTWKAGGTTV
TQGVETTKPS KQSNNRYAAS RYLALSASDW KFSSGFTCQV THEGTIVEKT
VTPSECA

PIGL4 Sequence

DSQTVIQEPAM SVSPGGTVALTCAFSSGSVT
TSNYPSWFQTPGQPPRQLIWRTNNRPTGV PGRFSGAISG NKAALTITGA
QANDEADYFCTLCKSTANVIFGGGTHLTVLGQPKAAPTVN LFPPSSEELG
TNKATLVCLI SDFYPGAVTV TWKAGGTTVT QGVETTKPSK QSNNRYAASR
YLALSASDWK FSSGFTCQVT HEGTIVEKTV TPSECA

Figure 9

A. PIGL1 sequence
```
LOCUS       PK              805 bp    DNA
BASE COUNT        168 A      264 C     221 G      152 T
ORIGIN
        1 GTGCCAAGGT   TGCATGCCTG   CAGGTCGACT   AGTACGGGGG   GGGGGGGGGG
GGGCAGGAGG
       61 CTAAAGAGGC   CCCTTCCCAA   AATTGTCCCC   ACCATGGCCT   GAACGGTGCT
TCTGATCGGG
      121 CTCCTCCCTG   TCGGCTCAGG   GGTGGATTCT   CAAACTGTGA   TCCAAAAACC
GGCAATCTCT
      181 TTTTCTCTTG   GAGGGACCGT   CACACTCACC   TGTGCCTTTA   GCTCTGGGTC
ACTCACTGGT
      241 ATTAACTACC   CTAGCTGGTT   CCAGCGGACA   CCAGGCCAGC   CTCCTCAAAC
TGTTATCTAC
      301 AACACAAACA   ACCGCCCGAC   TGGGGTCCCC   ATTCGCTTCT   CTGGAGCCAT
CTCTGGGAAC
      361 AAAGCCGCCC   TCACCATCAC   GGGGGCCCAG   GCTAAGGACG   AGGCCGACTA
CTTCTGTGCT
      421 CTGTATAAAA   GTAGCGCTCA   GATTACGTTC   GGCGGTGGGA   CCCATCTGAC
CGTCCTCGGT
      481 CAGCCCAAGG   CCGCTCCCAC   GGTCAACCTC   TTCCCGCCCT   CCTCTGAGGA
GCTCGGCACC
      541 AACAAGGCCA   CCCTGGTGTG   TCTAATAAGT   GACTTCTACC   CGGGCGCCGT
GACGGTGACC
      601 TGGAAGGCAG   GCGGCACCAC   CGTCACCCAG   GGCGTGGAGA   CCACCAAGCC
CTCGAAACAG
      661 AGCAACAACA   AGTACGCGGC   CAGCAGCTAC   CTGGCCCTGT   CCGCCAGTGA
CTGGAAATCT
      721 TCCAGCGGCT   TCACCTGCCA   GGTCACCCAC   GAGGGGACCA   TTGTGGAGAA
GACAGTGACG
      781 CCCTCCGAGT   GCGCCTAGGG   ATCCC
```

Figure 10A

B. PIGL2 sequence
LOCUS        PKG           751 bp    DNA
BASE COUNT        153 A      247 C      213 G      138 T
ORIGIN
       1 GGGGGGGGGC   TGAGGAGGCC   GCGTCCCAAG   ATTGTCCCCA   CCATGGCCTG
AACGGTGCTT
      61 CTGATCGGGC   TCCTCGCTGT   CGGCTCAGGG   GTGGATTCTC   AAACTGTGAT
CCAGGAGCCG
     121 GCGATGTCAG   TGTCTCCTGG   AGGGACCGTC   ACACTCACCT   GTGCCTTTAC
ATCTGGGTCA
     181 GTCACTACTA   GTAACCACCC   CGGCTGGTAC   CAGCAGACAC   CAGGCCAGCC
TCCCCGACTG
     241 GTGATTTACA   GGACAAACAA   CCGCCCGACT   GGGGTCCCCA   GTCGCTTCTC
TGGAGCCATC
     301 TCTGGGAACA   AAGCCGCCCT   CAGCATCACG   GGGGCCCAGG   CTAATGACGA
GGCCGACTAT
     361 TTCTGTACTC   TGTGGAAAGA   TAACACATAT   TTTTTCGGCG   GTGGGACCCG
TCTGACCGTC
     421 CTCGGTCAGC   CCAAGGCCGC   TCCCATGGTC   AATCTCTTCC   CGCCCTCCTC
TGAGGAGCTC
     481 GGCACCAACA   AGGCCACCCT   GGTGTGTCTA   ATAAGTGACT   TCTACCCGGG
CGCCGTGACG
     541 GTGACCTGGA   AGGCAGGCGG   CACCACCGTC   ACCCAGGGCG   TGGAGACCAC
CAAGCCCTCG
     601 AAACAGAGCA   ACAACAAGTA   CGCGGCCAGC   AGCTACCTGG   CCCTGTCCGC
CAGTGACTGG
     661 AAATCTTCCA   GCGGCTTCAC   CTGCCAGGTC   ACCCACGAGG   GGACCATTGT
GGAGAAGACA
     721 GTGACGCCCT   CCGAGTGCGC   CTAGGGATCC   C

Figure 10B

C. PIGL3 sequence
LOCUS           PPL2            657 bp
BASE COUNT      139 A      211 C      188 G      119 T
ORIGIN
        1 GTGGATTCTC    AGACTGTGAT    CCAGGAGCCG    GCGATGTCAG    TGTCTCCTGG
AGGGACCGTC
       61 ACAGTCACCT    GTGCCTTTAG    CTCTGGGTCA    GTCACTAGTA    GTGACTACCC
AAGCTGGTTC
      121 CAGCAGACAC    CAGGCCAGCC    TCCTCGAACT    GTCATCTACA    GAACAAACAA
GCCGCCCGAC
      181 TGGGTCCCAG    GTCTCTCTGG    AGCCATGTCT    GGGAACAAAG    CGTCCCTCAC
CATCACGGGG
      241 GCCCAGGCTG    AGGACGAGGC    TGACTACTTC    TGTGCTCTGG    AGGAAAAGTC
ACGGTATCAG
      301 GTTTTCGGCG    GTGGGACCCA    TTTGACCGTC    CTCGGTCAGC    CCAAGGCCGC
TCCCACGGTC
      361 AACTTCTTCC    CGCCCTCCTC    TGAGGAGCTC    GGCACCAACA    AGGCCACCCT
GGTGTGTCTA
      421 ATAAGTGACT    TCTACCCGGG    CGCCGTGACG    GTGACCTGGA    AGGCAGGCGG
CACCACCGTC
      481 ACCCAGGGCG    TGGAGACCAC    CAAGCCCTCG    AAACAGAGCA    ACAACAGGTA
CGCGGCCAGC
      541 AGGTACCTGG    CCCTGTCCGC    CAGTGACTGG    AAATTCTCCA    GCGGCTTCAC
CTGCCAGGTC
      601 ACCCACGAGG    GGACCATTGT    GGAGAAGACA    GTGACGCCCT    CCGAGTGCGC
CTAGGGA

Figure 10C

```
D. PIGL4 sequence
LOCUS       PPL4            687 bp   DNA
BASE COUNT        144 A      230 C     186 G      127 T
ORIGIN
       1 CCTGGACTCC   TCTCTCCTGT   TCGGGTGGAT   TCTCAGACTG   TGATCCAGGA
GCCGGCGATG
      61 TCAGTGTCTC   CTGGAGGGAC   CGTCGCACTC   ACCTGTGCCT   TTAGCTCTGG
GTCAGTCACT
     121 ACCAGTAACT   ACCCCAGCTG   GTTCCAGAAG   ACACCAGGCC   AGCCTCCCCG
ACAGCTGATC
     181 TGGAGAACAA   ACAACCGCCC   GACTGGGGTC   CCCGGTCGCT   TCTCTGGAGC
CATCTCTGGG
     241 AACAAAGCCG   CCCTCACCAT   CACGGGGGCC   CAGGCTAATG   ACGAGGCCGA
CTACTTTTGT
     301 ACTCTGTGTA   AAAGTACTGC   TAATGTAATT   TTCGGCGGTG   GGACCCATCT
GACCGTCCTC
     361 GGTCAGCCCA   AGGCCGCTCC   CACGGTCAAC   CTCTTCCCGC   CCTCCTCTGA
GGAGCTCGGC
     421 ACCAACAAGG   CCACCCTGGT   GTGTCTAATA   AGTGACTTCT   ACCCGGGCGC
CGTGACGGTG
     481 ACCTGGAAAG   CAGGCGGCAC   CACCGTCACC   CAGGGCGTGG   AGACAACCAA
GCCCTCGAAA
     541 CAGAGCAACA   ACAGGTACGC   GGCCAGCAGG   TACCTGGCCC   TGTCCGCCAG
TGACTGGAAA
     601 TTCTCCAGCG   GCTTCACCTG   CCAGGTCACC   CACGAGGGGA   CCATTGTGGA
GAAGACAGTG
     661 ACGCCCTCCG   AGTGCGCCTA   GGGACAC
```

Figure 10D

ANTIGENIZED ANTIBODY VACCINE FOR FOOT-AND-MOUTH DISEASE

BACKGROUND OF INVENTION

1) Field of Invention

The present invention relates to a vaccine which is capable of eliciting immunicity against foot-and-mouth disease.

2) Description of Prior Art

Antibodies are proteins produced by the body's immune system in response to foreign elements known as antigens, which invade the body. Vaccine can elicit an immune response, which subsequently protects the host from infection by the disease-causing agents (antigens).

Usually, the vaccine consists of the organism or parts of the thereof that causes the disease. The organism or some parts of it, which makes up the vaccine is often killed or attenuated, so that the disease-causing organism will lose some or all of its ability to cause disease in the host. In most cases, bacteria, and to some extent viruses, slowly lose their ability to colonize living things as they are cultured outside the body.

There are a number of approaches to producing vaccines, and the major kinds of vaccines include viral vaccines, biopharmaceutical vaccines, multiple antigen-peptide vaccines and polyprotein vaccines.

Foot-and-Mouth Disease, also known as FMD hereinafter, is a highly contagious, severely debilitating disease that infects all cloven-hoofed animals. It is endemic in many developing countries worldwide. In particular, swine in Asian have often been affected by FMD. FMD reduces livestock productivity, incurs high vaccination costs, and restricts the international trade of livestock and livestock products. FMD is a viral infectious disease and the foot-and-mouth disease virus, also known as FMDV hereinafter, is a small animal virus having a single stranded positive sense RNA genome of about 8,000 nucleotides.

Two major types of vaccines have been produced against FMD. They are conventional vaccines and synthetic peptide vaccines. Conventional vaccines against FMDV use either inactivated FMD virus or a live attenuated FMD virus. The conventional vaccine approach, although generally effective, have several undesirable drawbacks associated with it.

Firstly, it is cost inefficient. This type of vaccine is made from large amounts of live, infectious virus. Maintaining and processing a large quantity of infectious virus is expensive, labor intensive and space inefficient.

Second and most importantly, these vaccines are potentially dangerous. Most of the outbreaks of FMD in recent years have been caused either by the escape of virus from vaccine production units or the use of incompletely inactivated or insufficiently attenuated virus. For example, during the 1980's, a number of outbreaks occurred in European countries including Italy, United Kingdom, France and in Taiwan in 1996. As the causative viruses of outbreaks were often found to be closely related or even identical to the strains that were used in Europe for manufacturing, it is possible that the primary outbreaks were caused by inadequately inactivated vaccines or by virus that escaped from vaccine production plants.

Another problem associated with producing conventional vaccine is that they are thermolabile. Conventional FMD vaccines are relatively unstable when exposed to elevated temperatures and they have to be stored at low temperatures. Constantly maintaining the required low temperatures is often not easily achievable, especially in tropical countries.

An addition potential problem in a virus culturing procedure of the conventional vaccine production vaccine production process is the use of fetal bovine serum virus culturing. It is possible that diseases can be introduced from the fetal bovine serum and affect the vaccinated animals.

Yet another major disadvantage of using conventional FMD vaccines is that most vaccines produced using the conventional method are relatively crude preparations of inactivated tissue culture grown virus. This tissue cultural mix may cause serious side effects such as allergic responses and abortions in susceptible stock.

There are newer forms of FMDV vaccines that do not use inactivated virus. They are synthetic peptide vaccines and recombinant protein vaccines. The identification of the immuno-dominant sites on viral protein 1 (VP1) of FMDV provided new ideas for designing synthetic peptide and recombinant protein FMD vaccines. Compared to conventional vaccines, these two types of vaccines are both safe in production and application. They are also very easy to handle, store, transport and can be designed to meet specific requirements.

The study of synthetic FMDV peptide vaccine was started by polymerizing the 141 a.a.–160 a.a. peptide from VP1 with either glutaraldehyde or air-oxidized after a cysteine residue was added at each terminus. It was found that uncoupled peptides could be made immunogenic. In 1987, Francis and his colleagues reported that the presence of C-terminal cysteines with a free thiol group largely enhanced the immunogenicity of free 141–160 a.a. peptide. Similar results were also obtained when multiple cysteine residues were added. It was suggested that the presence of a free thiol cysteine residue would allow the formation of peptide dimers leading to a more ordered secondary structure causing immune complex formation in vivo (Francis, 1995). According to this idea, immunogenicity of tandem repeats (Cys 137–162(×2)) was compared to that of a single copy of Cys 137–163 peptide. It was found that tandem repeats of the FMDV peptide were generally more immunogenic than the single copy of disulphide dimers. The addition of a cysteine residue could result in the formation of disuphide tetramer structures which improved the immune response further.

The concept of multiple copies synthetic peptides was further tested by using Tam's multiple antigenic peptide (MAP) system (Tam 1988). This system allows solid phase synthesis of a peptide antigen onto a branching lysine backbone to produce several polylysine octamer constructs. This system where there are multiple copies of the peptide resulted in greatly enhanced response.

In order to apply multiple copies of the FMDV peptide, recombinant DNA technology has been applied by fusing small peptide sequences to the gene coding for larger proteins. These larger proteins of recombinant vaccine have a number of characteristics. The goal of linking the peptide to the carrier is to provide a completely uniform and defined structure for the presentation of the immunogens as compared with those prepared by chemical cross-linking (Francis, 1991). This approach was first investigated by fusing single or multiple copies of the FMDV immunogenic peptides to the N-terminus of a bacterial protein, beta-galactosidase (Broekhuijsen et al., 1986; Winther et al., 1986). Beta-galactosidase was chosen because it has been shown that antibodies can be elicited against the epitopes from VP1 that are located at the N-terminus, and it also contains several T cell epitopes (Krzych et al., 1982; Manca et al., 1985). The immunogenicity of this multiple copy FMDV peptide-beta-galactosidase recombinant protein is found to be similar to that obtained from using the lysine background system (Broekhuijen et al., 1987).

Multiple peptide presentation was then further developed using FMDV peptide sequence fused to the N-terminus of the hepatitis B virus core antigen (HBcAg) to produce HBc fusion particles. It was reported that this 27 nm hybrid protein particle was able to give full protection to guniea pigs with results that were close to that elicited by inactivated FMDV VP1 142 a.a.–160 a.a. peptide and could protect animals against challenge infections.

Although initially promising, the synthetic peptide approach and recombinant protein vaccine approach appear to have shortcomings. Among these are poor predictability of the tertiary structure and weak immnunogenicity. Peptides in solution exist in conformations that may not be always optimal for receptor binding (B-cell receptor and possibly T-cell receptor and major histocompatibility gene products) if specific conformation at the three-dimensional level is required for it to exhibit its intended functions.

In the case in which synthetic peptides that are relatively small in size, they tend to be easily degraded in the body after injection. Therefore, they may not be very effective in providing long term immune response probably because the recombinant protein vaccine fails to exhibit a proper conformation. Also, peptide synthesis is expensive which may lead to high production cost of the vaccine. As mentioned, presentation of the FMDV epitopes on peptide vaccines can be achieved by fusing them to the N-terminus of microbial proteins like beta-galactosidase or HBcAg. However, using beta-galactosidase may elicit a lot of additional and undesirable immune responses (Bona et al., 1994). After repetitive immunization of this recombinant protein vaccine, side effects may occur such as immediate hypersensitivity that can cause severe hay fever and asthma in the animal.

Nucleic acid vaccines or DNA vaccine represent a new approach to the control of infectious agents. These novel vaccines are easier to design and manufacture. Recombinant DNA technology is used to clone DNA sequences encoding the protein or proteins to be used as immunogens into an eukaryotic expression vector.

Antigenized antibodies are antibodies which are genetically engineered in their variable domains to express epitopes of different antigens. Antigenized antibodies can be used as immunogens that focus the immune response on specific B- or T-cell epitopes. As such, antigenized antibodies can be used as an alternative approach to conventional or synthetic peptide vaccination.

Therefore, the most effective kind of vaccine that offers both the possibilities of safety and efficiency is the antigenized antibody vaccine. The process of antibody antigenization consists of grafting peptide epitopes derived from antigens other than immunoglobulins into complementarity determining region ("CDR") loops of an antibody molecule. Because the CDR loops are exposed at the surface of the antibody molecule, they provide the major contribution to antibody antigenicity. Unlike the synthetic vaccines described above, antigenized antibodies target antigen-presenting cells via the Fc receptor, thereby maximizing antigen presentation by class II major hisocompatibility (MHC) molecules. Also, antigenized antibodies provide B-cells with a continuous source of antigenic peptides for presentation in class I MHC molecules. In addition to immunogenicity at the B-cell level, antigenized antibodies act as processed peptide products to generate Th-cell immunogenicity.

OBJECT OF THE INVENTION

Accordingly, it is an object of the present invention to provide antigenized antibody vaccines against Foot-and-Mouth disease to provide a safer, more cost efficient and/or more effective vaccine product which can overcome some of the disadvantages of the prior art, and provide the public with a useful choice.

SUMMARY OF INVENTION

The present invention can be used against FMD in swine, although by using FMDV viral epitopes for cows linked to cow IgG, this vaccine can be applied in other animals like cows as well.

The present invention consists of a vaccine of which its functions can be delivered in four different forms, namely two constructs of protein vaccine and two correlative constructs of DNA vaccine counterparts. All forms of this vaccine deliver the functions of immunization against FMD and FMDV in swine. To be specific, the vaccine in its protein forms are an antigenized antibody vaccine; this peptide sequence contains FMDV epitopes that replace CDR loops in swine IgG or a chimeric protein which FMDV single or tandem repeat epitopes carried by swine IgG heavy chain constant region protein.

As an example shown, the particular FMDV epitopes used for grafting into CDR engineered. The first form of the DNA counterpart that corresponds to the first form of the protein vaccine utilizes FMDV epitope cDNA sequences as the carrier for single IgG in plasmid form. The second form of the DNA counterpart that corresponds to the second form of the protein vaccine utilizes FMDV epitope DNA sequences linked differently with the heavy chain constant region of swine Ig cDNA. Further, immunization methods of swine against FMD or FMDV are carried out by the use of this vaccine. There are different ways in which this vaccine can be administered. For the protein forms of the vaccine, it can be, for example, administered through conventional injection. In the case of administering the vaccine in its DNA forms, it can be carried out by using epidermis gene gun or injection.

BRIEF DESCRIPTION OF THE DRAWINGS

A preferred embodiment of the present invention will now be explained, by way of example and with reference to the accompanying drawings in which:

FIG. 3 shows the amino acid sequence (SEQ ID NO: 1) of the antigenized antibody heavy chain molecule in which the CDR3 region is replaced with FMDV VP1 aa 200 to 213;

FIG. 4 shows the corresponding cDNA sequence (SEQ ID NO:2) of the amino acid mentioned in FIG. 3;

FIG. 5 shows the amino acid sequence (SEQ ID NO:3) of the antigenized antibody heavy chain molecule in which the CDR3 is replaced with FMDV VP1 aa 141 to 160;

FIG. 6 shows the corresponding cDNA sequence (SEQ ID NO: 4) of the amino acid mentioned in FIG. 5 and the bold part shows the FMD sequence (SEQ ID NO: 21).

FIG. 7 shows the cDNA sequence (SEQ ID NO: 5) of antigenized chimeric vaccine molecule. The bold part shows the epitopes of FMDV VP1 (aa 141 to 160, aa 200 to 213) (SEQ ID NO: 22). The rest of the sequence belongs to PIG IgG heavy chain constant region.

FIG. 8 shows the protein sequence (SEQ ID NO: 6) of antigenized chimeric vaccine molecule. The bold part shows the epitopes of FMDV VP1 (aa 141 to 160, aa 200 to 213). The rest of the sequence belongs to PIG IgG heavy chain constant region.

FIG. 9 shows four amino acid sequences of which the light chain of IgG can be coded for. The bolded sequences are the framework regions. The underlined sequences are the CDR regions. The CDR2 or CDR3 sequence could be replaced by correspondence FMDV epitope sequences;

FIGS. 10A–10D show the four cDNA sequences corresponding to the cDNA sequences of the IgG light chain in FIG. 8;

DETAILED DESCRIPTION OF THE INVENTION

The present invention is based on a new kind of vaccine against FMD. This new kind of vaccine can elicit immune response against FMD. The present invention consists of an engineering of cDNA sequence encoding for FMDV epitopes. The vaccine also contains swine IgG cDNA construct as a carrier for the FMDV epitopes. The conjugation of the FMDV epitopes and swine IgG in its protein forms are carried out by grafting of FMDV peptide epitopes into swine IgG CDR loops or link FMDV epitopes with the swine IgG constant region as shown in FIG. 1b.

Figure 1A:
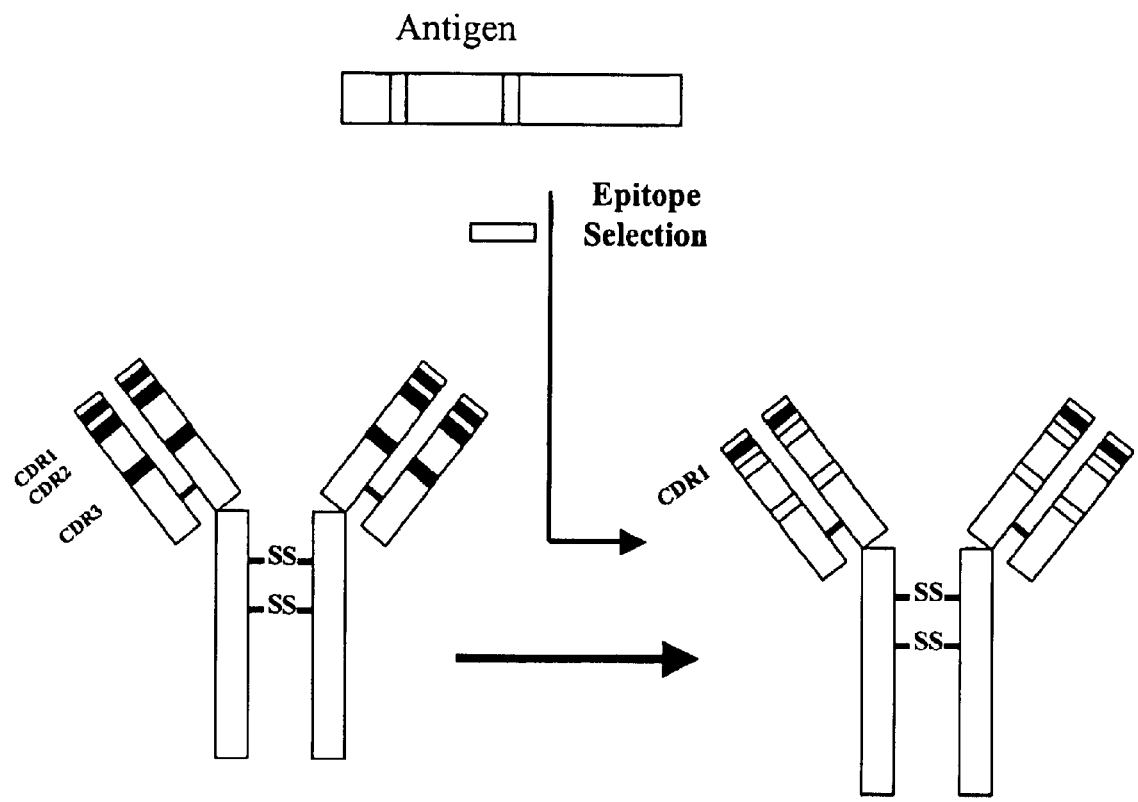
FIG. 1a shows the diagrammatic structure of the antigenized antibody vaccine using swine IgG.
Figure 1B:
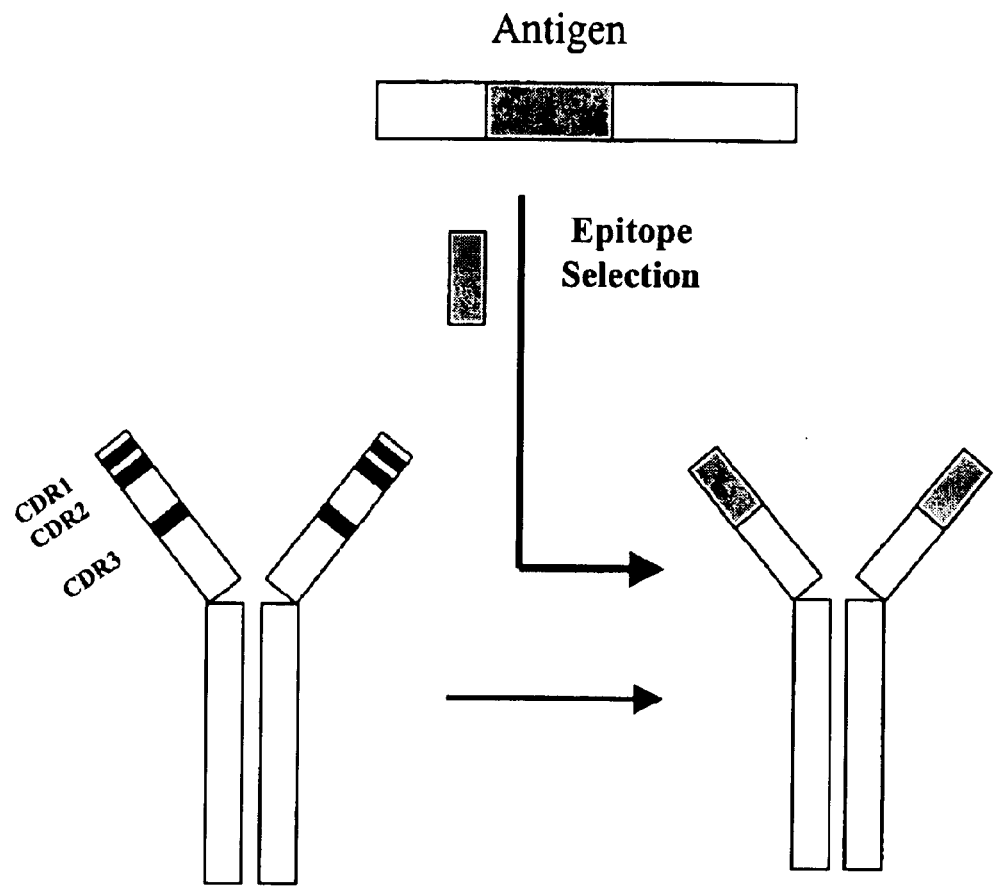
FIG. 1b shows the diagrammatic structure of the antigenized chimeric vaccine using FMDV single or tandem repeat epitopes.
Figure 2A:
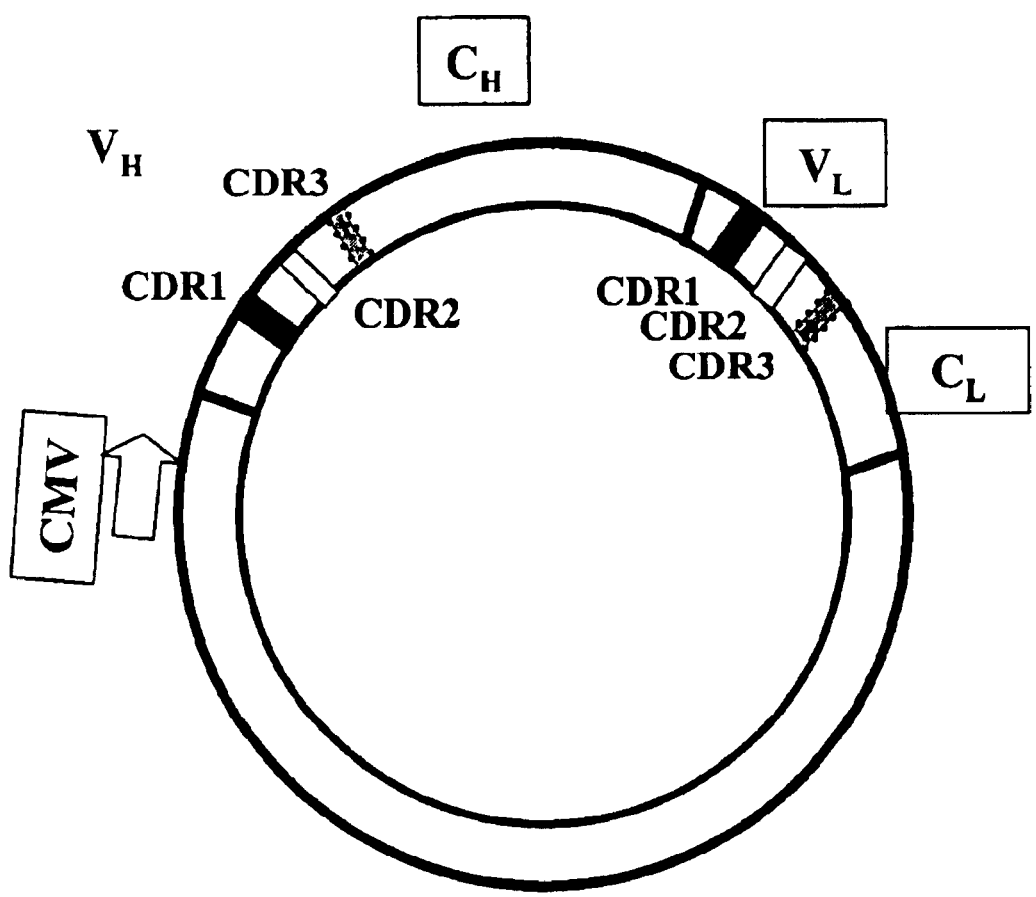
FIG. 2a shows the corresponding cDNA of the antigenized antibody vaccine, which uses IgG cDNA as a carrier in the plasmid.
Figure 2B:
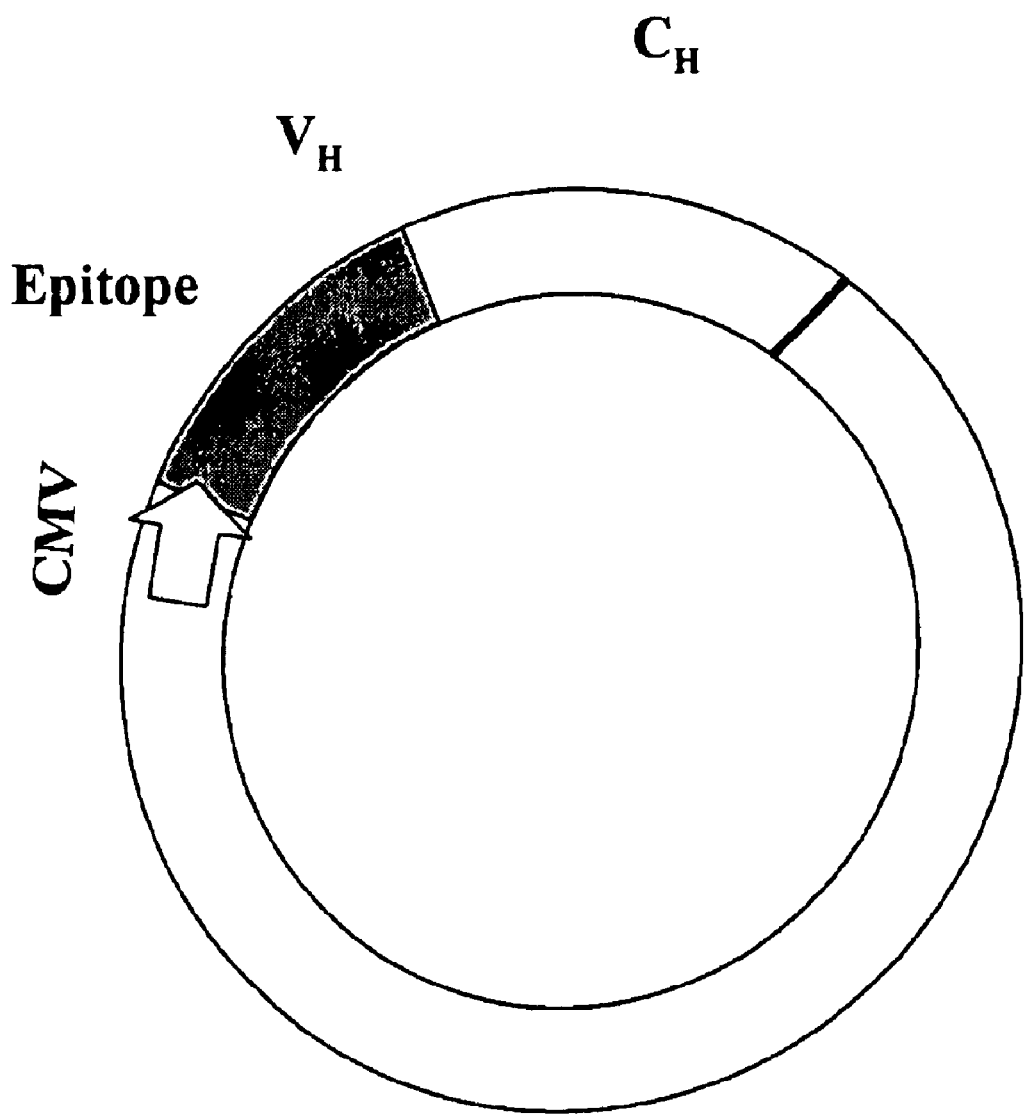
FIG. 2b shows the corresponding cDNA of the antigenized chimeric vaccine using FMDV single or tandem repeat epitopes.

Therefore, the antigenized antibody vaccine molecules in its protein form are created from the grafting of peptide epitopes derived from FMDV into swine antibody CDR loops, as shown in FIG. 1a and 1b. FMDV peptide epitopes were synthesized by PCR based on VP1 gene of FMDV. The overlapping PCR method was used to insert the FMDV peptide epitopes into the CDR regions of swine immunoglobulin heavy and light chain genes. The resulting antigenized antibody genes were cloned into mammalian expression vector. The plasmids were transfected into CHO or myeloma cells.

The present invention of vaccine actually has two preferred types, and each type has two preferred forms. Therefore, the present invention has a total of four different embodiments discussed herein as illustrated in FIG. 1a, 1b and FIG. 2a, 2b. Two of them are protein forms (FIG. 1a, 1b), known as antigenized antibody vaccines that can be administered by injection. The first type is the antigenized antibody vaccine that utilizes swine IgG protein as the carrier for FMDV epitopes and is injected into swine muscle tissue. The first form of this antigenized antibody vaccine (FIG. 1a) inserts the FMDV epitopes into the CDR2 and CDR3 regions of both heavy and light chains swine IgG. The second form of this antigenized antibody vaccine (FIG. 1b) utilizes single or tandem-repeat FMDV epitopes linked to only the heavy chain constant region of swine IgG, forming a chimeric protein. Hence, the second form of this antigenized antibody vaccine can also be called as antigenized chimeric vaccine.

The second type of the present invention is called naked DNA vaccines, which can be administered through gene gun shooting. Each DNA form has a corresponding protein form counterpart. There are two forms of this naked DNA vaccine that correspond to their protein counterparts as mentioned above. The two DNA forms will be expressed by the host's cell machinery after being administered. The corresponding protein equivalents will be directly administered into the animal, which have the same functions as the naked DNA vaccine forms. The first form of this naked DNA vaccine grafts FMDV epitope DNA sequences onto the CDR2 and CDR3 regions of both heavy and light chain swine IgG cDNA. The second form of this DNA vaccine utilizes FMDV epitope DNA sequences (FIG. 4) linked only with the heavy chain constant region of swine IgG cDNA. The two forms of naked DNA vaccine will exhibit the functions of the two forms of antigenized antibody vaccine respectively, when the transcription and translation process produce the products within the host cell machinery.

Methods

The construction of the vaccine involves three major steps, namely 1) cloning of the swine single IgG heavy chain constant region, and swine light chain 2) joining of the two FMDV immunogenic sequences and 3) joining of the swine IgG single heavy chain constant region with the FMDV immunogenic sequence, then insert it into bacterial expression vector. The details of the procedures involved are explained as follow.

1) Cloning of the Swine Single IgG Heavy Chain Constant Region

The extraction and purification of mRNA from swine spleen was done by using a commercially available kit (mRNA Preparation kit, by Pharmacia). The procedures were followed as described by the manufacturer. In brief, 3 g of fresh swine spleen was homogenized in 1.2 ml Extraction Buffer. The homogenized tissue extract was diluted by 2.4 ml Elution Buffer and was mixed thoroughly. The homogenate was transferred to a sterile tube and centrifuged for one minute to obtain cleared homogenate. 1 ml of the cleared homogenate was placed on the top of the Oligo(dT)-Cellulose pellet. The Oligo(dT)-Cellulose was resuspended by inverting the tube for 3 minutes. The pellet was collected by centrifugation at 16,000×g for 10 seconds. For washing, the Oligo(dT)-Cellulose was washed five times with 1 ml High-Salt Buffer and centrifuged at 16,000×g for 10 seconds, followed with washing three times with 1 ml Low-Salt Buffer and centrifuged at 16,000×g for 10 seconds. Then the pellet was resuspended in 0.3 ml Low-Salt Buffer and transferred to a MicroSpinTM Column. The column was centrifuged at full speed for 5 seconds. The effluent was discarded and a new collection tube was put in place. This step was repeated twice. The column was placed in a sterile microcentrifuge tube and 0.2 ml pre-warmed Elution Buffer was added. The eluate containing mRNA was collected by centrifugation at full speed for 5 seconds. 10 ml of Glycogen Solution and 1/10 volume of Potassium Acetate Solution was added to the sample. The sample was mixed with 500 ml 100% ethanol and placed at −20° C. for at least 30 minutes. The precipitated mRNA was collected by centrifugation at 14,000 rpm at 4° C. for 5 minutes. The supernatant was discarded and the precipitated mRNA was dissolved in DEPC-treated water. The quantity of RNAs was determined by UV absorbance at 260 nm.

RT-PCR Analysis

The cDNA fragments encoding the constant region of the heavy chain of the swine IgG were amplified by RT-PCR using a set of swine IgG 5' and 3' specific primers. Swine IgG 3' specific primers were used to prime the first strand cDNA synthesis from total RNA. Reverse transcription was carried out at 37° C. for 60 minutes by MMLV reverse transcriptase and terminated at 70° C. for 15 minutes. The cDNA products were amplified by PCR in the presence of swine IgG 5' specific primer. The PCR settings were as follows and ran for 30 cycles: denaturing at 94° C. for 1 min, annealing at 50° C. for 1 min and extension at 72° C. for 2 min, with a final extension at 72° C. for 6 min. The PCR products were fractionated on 1.0% low melting agarose gel and the band with sizes corresponding to the constant region of the IgG heavy chain was purified from the gel using phenol:chloroform extraction and ethanol precipitation. The DNA was then ligated to the FMDV immunogenic sequences (F1) later.

The PCR primers used were designed from swine IgG genes (Kacskovics et al., 1994) and the sequence of the primers are as listed below:

```
Swine IgG 3' specific primer: (SEQ ID NO:15)
5'GAC GCT CGA GTC ATC ATT TAC CCT GAG T 3'
Swine IgG 5' specific primer: (SEQ ID NO: 16)
5'AGC TAA GCT TGC CCC CAA GAC GGC CCC A 3'
```

2) Joining of the Two FMDV Immunogenic Sequences

Two oligonucleotide sequences were made corresponding to the residues 141–160 and 200–213 (two sequences were made with residues 155–160 sequence as overlapping region) on the VP1 of FMDV (Kurz et al., 1981). The two sequences were joined by overlapping PCR. The setting was as follows and ran for 5 cycles: 94° C. for 1 minute, 63° C. for 3 minutes. Two primers, VP1 3' primer and VP1 5' primer, were used to add in one Hind III restriction site at the 3' end and one Nde I restriction site at the 5' end. The PCR setting was as follow and ran for 24 cycles: denaturing at 94° C. for 1 minute, annealing at 50° C. for 1 minute, extension at 72° C. for 2 minutes and final extension at 72° C. for 6 minutes. The PCR product was analyzed on 1.5% low melting agarose gel. Product with correct size was cut and purified. The joined fragment was called FMDV-immuno-sequence. The VP1 3' and 5' primers used were designed from VP1 141 a.a.–160 a.a. and 200 a.a.–213 a.a. (Kurz et al., 1981). Sequences of the primers are as listed below:

```
VP1 5' primer: (SEQ ID NO:17)
5' ATG CCA TAT GGT ACC AAA C 3'
VP1 3' primer: (SEQ ID NO:18)
5' ATG CAA GCT TCA ACT TCT G 3'
```

Figure 11A:
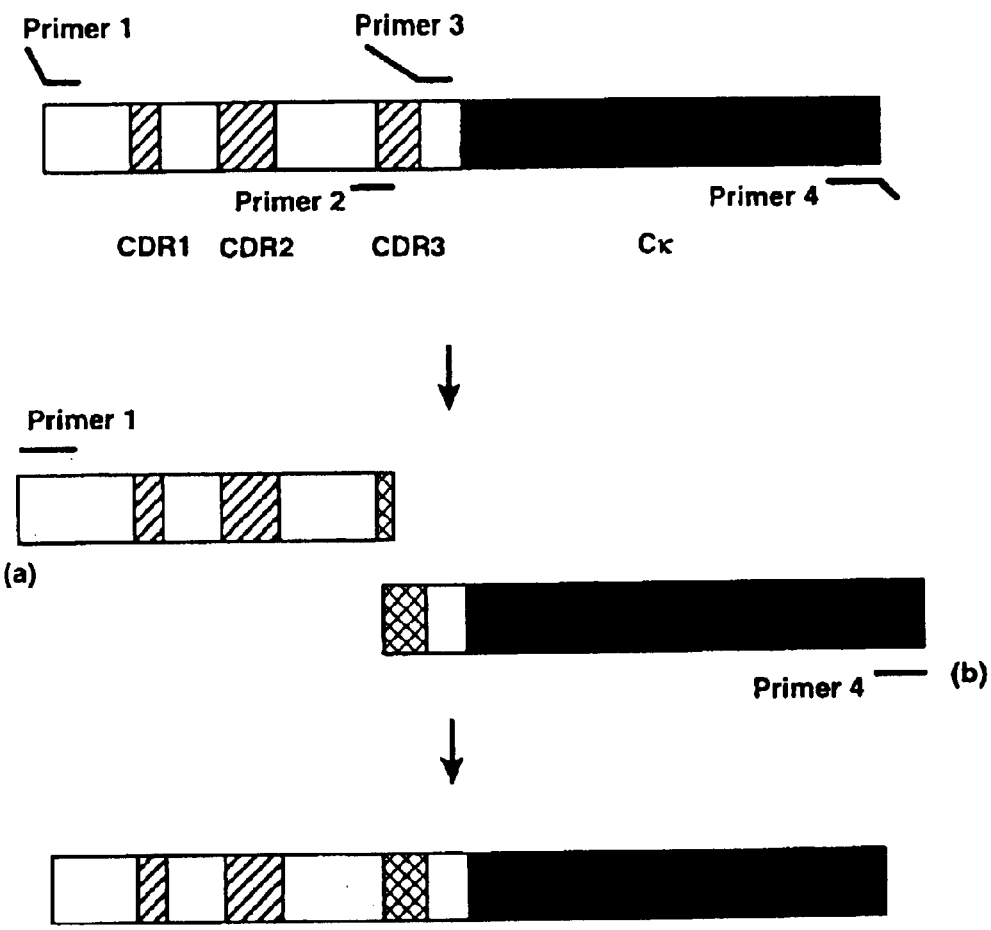
FIG. 11A shows the overlapping (extension) PCR taking place.
Figure 11B:
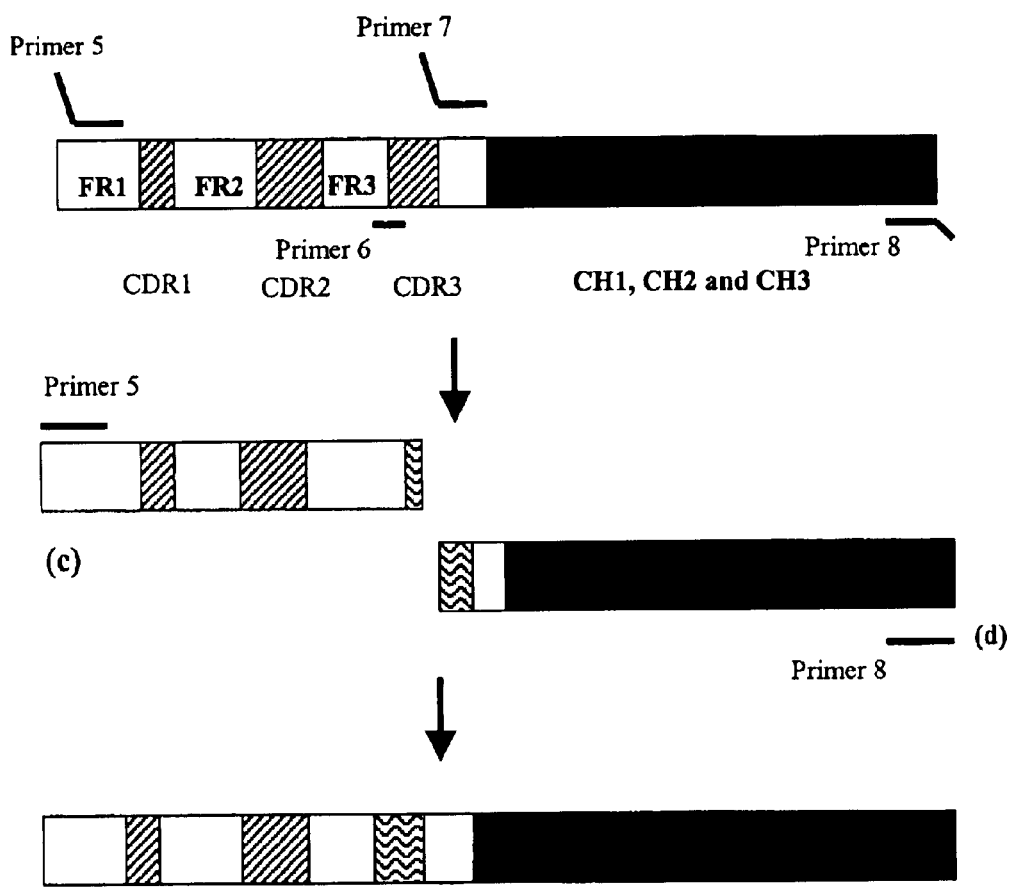
FIG. 11B shows the overlapping (extension) PCR taking place.

FIG. 11a illustrates the overlap(extension) PCR taking place in two stages. First, the CDR1/CDR2 region is amplified, as is the CH/CDR3 region. The oligonucleotides at CDR3 are complementary; the longer primer 3 also contains VP1 141–160 or 200–213 residues. This permits fusion of these two products (a and b) in a subsequent PCR. FIGS. 11B illustrates the overlap (extension) PCR takes palce in two stages. First, the CDR1/CDR2 region is amplified, as is the CH/CDR3 region. The oligos at CDR3 are complementary; the longer primer 7 also contains VP1 141–160 or 200–213 residues. This permits fusion of these two products (c and d) in a subsequent PCR.

3) Linking of the Swine IgG Single Heavy Chain Constant Region, the FMDV-immuno-sequence Fragment and the Bacterial Expression Vector The above fragment was digested with Nde I and Hind III; the swine single IgG heavy chain constant region was digested with Hind III and Xho I, and the bacterial expression vector was digested with Nde I and Xho I. The three digested fragments were purified by phenol/chloroform extraction and ethanol precipitation. They were then ligated by using T4 DNA ligase at 16° C. overnight. The ligation product was transformed into JM109 and colonies were screened by mini-plasmid isolation and then by restriction enzyme digestion. Plasmid from correct clone was isolated and checked by DNA sequencing. Finally, the correct plasmid was transformed into E. coli BL(21)DE3pLysE. The plasmid was named as pF1-IgG.

Thus, the present invention can provide an antigenized antibody vaccine against Foot-and-Mouth disease to provide a safer, more cost efficient and/or more effective vaccine product which can overcome some of the disadvantages of the prior art.

The invention as described is deemed to incorporate equivalents to the integers recited where such equivalents would be apparent to those skilled in the art. The description is provided by way of example and is not to be considered limited to the scope of the invention which is defined in the appended claims.

What is claimed is:

1. A nucleotide sequence encoding antigenized swine antibodies that carry Foot-and-Mouth Disease, FMD, epitopes said nucleotide sequence including a first nucleotide sequence encoding heavy chain constant region of swine IgG; and a second nucleotide sequence comprising
SEQ ID NO: 20;
SEQ ID NO: 21; or
SEQ ID NO: 22.

2. The nucleotide sequence of claim 1 comprising
SEQ ID NO: 2;
SEQ ID NO: 4; or
SEQ ID NO: 5.

3. The nucleotide sequence as claimed in claim 1 further including a third nucleotide sequence encoding a modified light chain of swine IgG.

4. The nucleotide sequence of claim 3, wherein the third nucleotide sequence comprises
SEQ ID NO: 11;
SEQ ID NO: 12;
SEQ ID NO: 13; or
SEQ ID NO: 14.

5. A method for manufacturing a nucleotide sequence encoding antigenized swine antibodies that carry Foot-and-Mouth Disease, FMD, epitopes, including the steps of: cloning a first nucleotide sequence encoding heavy chain constant region of swine IgG; and
joining a second nucleotide sequence encoding FMD epitopes said nucleotide sequence comprising:
SEQ ID NO: 20;
SEQ ID NO: 21; or
SEQ ID NO: 22
to the first nucleotide sequence.

6. The method as claimed in claim 5, wherein the first nucleotide sequence is cloned by utilizing a set of swine IgG 5' and 3' primers comprising:

SEQ ID NO: 16 and
SEQ ID NO: 15.

7. The method as claimed in claim 5, wherein the second nucleotide is joined to the first nucleotide sequence by utilizing either a viral protein 1, VP1, or FMD virus primer comprising:

SEQ ID NO: 17 or
SEQ ID NO: 18.

8. The method as claimed in claim 5, wherein the nucleotide sequence encoding comprises:

SEQ ID NO: 2;
SEQ ID NO: 4, or
SEQ ID NO: 5.

9. The method of claim 5, further including the step of joining a third nucleotide sequence encoding a modified light chain of swine IgG to the first nucleotide sequence.

10. The method of claim 9, wherein the third nucleotide sequence comprises

SEQ ID NO: 11;
SEQ ID NO: 12;
SEQ ID NO: 13, or
SEQ ID NO: 14.

11. A nucleotide sequence encoding Foot-and-Mouth Disease FMD, epitope wherein said nucleotide sequence is selected from the group consisting of:

SEQ ID NO: 2;
SEQ ID NO: 4; and
SEQ ID NO: 5.

12. A nucleotide sequence for the manufacturing of a nucleotide sequence encoding antigenized swine antibodies that carry Foot-and-Mouth Disease, FMD, epitopes wherein said nucleotide sequence is selected from the group consisting of:

SEQ ID NO: 15;
SEQ ID NO: 16;
SEQ ID NO: 17; and
SEQ ID NO: 18.

* * * * *

UNITED STATES PATENT AND TRADEMARK OFFICE
CERTIFICATE OF CORRECTION

PATENT NO. : 6,774,225 B2
DATED : August 10, 2004
INVENTOR(S) : Xie Yong

It is certified that error appears in the above-identified patent and that said Letters Patent is hereby corrected as shown below:

Column 3,
Line 9, delete "(IIBcAg)" and insert in lieu thereof -- (HBcAg) --;
Line 9, delete "IIBc" and insert in lieu thereof -- HBc --;

Column 8,
Line 13, delete "CII" and insert in lieu thereof -- CH --;
Line 18, delete "palce" and insert in lieu thereof -- place --;
Line 26, delete "IIind" and insert in lieu thereof -- Hind --.

Signed and Sealed this

Eighth Day of February, 2005

JON W. DUDAS
*Director of the United States Patent and Trademark Office*

SEQUENCE LISTING

```
<160> NUMBER OF SEQ ID NOS: 22

<210> SEQ ID NO 1
<211> LENGTH: 470
<212> TYPE: PRT
<213> ORGANISM: Sus sp.

<400> SEQUENCE: 1

Met Glu Phe Arg Leu Asn Trp Val Val Leu Phe Ala Leu Leu Gln Gly
 1               5                   10                  15
```

-continued

```
Val Gln Gly Glu Glu Lys Leu Val Glu Ser Gly Gly Leu Val Gln
             20                  25                  30
Pro Gly Gly Ser Leu Lys Leu Ser Cys Val Gly Ser Gly Phe Thr Phe
             35                  40                  45
Ser Ser Thr Tyr Ile His Trp Val Arg Gln Ala Pro Gly Lys Gly Leu
 50                  55                  60
Glu Trp Leu Ala Gly Leu Tyr Ser Ser Thr Pro Thr Tyr Tyr Ser
 65                  70                  75                  80
Asp Ser Val Lys Gly Arg Phe Asp Ile Ser Arg Glu Asp Ala Gln Asn
                 85                  90                  95
Thr Ala Tyr Leu Gln Met Asn Gly Leu Lys Thr Glu Asp Thr Ala Arg
            100                 105                 110
Tyr Tyr Cys Gly Lys Arg His Lys Gln Glu Ile Val Ala Pro Val Lys
            115                 120                 125
Gln Lys Leu Trp Gly Pro Gly Val Glu Val Val Ser Ser Ala Pro
130                 135                 140
Lys Thr Ala Pro Ser Val Tyr Pro Leu Ala Pro Cys Gly Arg Asp Val
145                 150                 155                 160
Ser Gly Pro Asn Val Ala Leu Gly Cys Leu Ala Ser Ser Tyr Phe Pro
                165                 170                 175
Glu Pro Val Thr Val Thr Trp Asn Ser Gly Ala Leu Thr Ser Gly Val
            180                 185                 190
His Thr Phe Pro Ser Val Leu Gln Pro Ser Gly Leu Tyr Ser Leu Ser
            195                 200                 205
Ser Met Val Thr Val Pro Ala Ser Ser Leu Ser Ser Lys Ser Tyr Thr
            210                 215                 220
Cys Asn Val Asn His Pro Ala Thr Thr Thr Lys Val Asp Lys Arg Val
225                 230                 235                 240
Gly Ile His Gln Pro Gln Thr Cys Pro Ile Cys Pro Gly Cys Glu Val
                245                 250                 255
Ala Gly Pro Ser Val Phe Ile Phe Pro Pro Lys Pro Lys Asp Thr Leu
            260                 265                 270
Met Ile Ser Gln Thr Pro Glu Val Thr Cys Val Val Val Asp Val Ser
            275                 280                 285
Lys Glu His Ala Glu Val Gln Phe Ser Trp Tyr Val Asp Gly Val Glu
290                 295                 300
Val His Thr Ala Glu Thr Arg Pro Lys Glu Glu Gln Phe Asn Ser Thr
305                 310                 315                 320
Tyr Arg Val Val Ser Val Leu Pro Ile Gln His Gln Asp Trp Leu Lys
                325                 330                 335
Gly Lys Glu Phe Lys Cys Lys Val Asn Asn Val Asp Leu Pro Ala Pro
            340                 345                 350
Ile Thr Arg Thr Ile Ser Lys Ala Ile Gly Gln Ser Arg Glu Pro Gln
            355                 360                 365
Val Tyr Thr Leu Pro Pro Ala Glu Glu Leu Ser Arg Ser Lys Val
370                 375                 380
Thr Leu Thr Cys Leu Val Ile Gly Phe Tyr Pro Pro Asp Ile His Val
385                 390                 395                 400
Glu Trp Lys Ser Asn Gly Gln Pro Glu Pro Glu Asn Thr Tyr Arg Thr
                405                 410                 415
Thr Pro Pro Gln Gln Asp Val Asp Gly Thr Phe Phe Leu Tyr Ser Lys
            420                 425                 430
```

```
Leu Ala Val Asp Lys Ala Arg Trp Asp His Gly Asp Lys Phe Glu Cys
        435                 440                 445

Ala Val Met His Glu Ala Leu His Asn His Tyr Thr Gln Lys Ser Ile
    450                 455                 460

Ser Lys Thr Gln Gly Lys
465                 470

<210> SEQ ID NO 2
<211> LENGTH: 1505
<212> TYPE: DNA
<213> ORGANISM: Sus sp.

<400> SEQUENCE: 2
atggagtttc ggctgaactg ggtggtcttg tttgctctct tacaaggtgt ccagggtgag      60
gagaagctgg tggagtctgg aggaggcctg gtgcagcctg gggggtctct gaaactctcc     120
tgtgtcggct ctggattcac cttcagtagt acctatattc actgggtccg ccaggctcca     180
gggaagggac tggagtggct ggcaggtctc tacagtagta ctacgccgac ctactactca     240
gactctgtga aggccggttt cgacatctcc agagaggacg cccagaacac ggcctatcta     300
caaatgaacg gcctgaaaac cgaagacacg gcccgctact actgtggaaa gcgtcacaaa     360
caggaaatcg tagctccagt aaaacagaag ttgtggggcc caggcgttga agtcgtcgtg     420
tcctcagccc ccaagacggc cccatcggtc taccctctgg cccctgcgg cagggacacg      480
tctggcccta acgtggcctt gggctgcctg gcctcaagct acttccccga gccagtgacc     540
atgacctgga actcgggcgc cctgaccagt ggcgtgcaca ccttcccatc cgtcctgcag     600
ccgtcagggc tctactccct cagcagcatg gtgaccgtgc cggccagcag cctgtccagc     660
aagagctaca ccctgcaatg tcaaccaccc gccaccacca ccaaggtgga caagcgtgtt     720
ggaatacacc agccgcaaac atgtcccata tgcccaggct gtgaagtggc cgggccctcg     780
gtcttcatct tccctccaaa acccaaggac accctcatga tctcccagac ccccgaggtc     840
acgtgcgtgg tggtggacgt cagcaaggag cacgccgagg tccagttctc ctggtacgtg     900
gacggggtag aggtgcacac ggccgagacg agaccaaagg aggagcagtt caacagcacc     960
taccgtgtgg tcagcgtcct gcccatccag caccaggact ggctgaaggg gaaggagttc    1020
aagtgcaagg tcaacaacgt agacctccca gcccccatca cgaggaccat ctccaaggct    1080
atagggcaga gccgggagcc gcaggtgtac accctgcccc cacccgccga ggagctgtcc    1140
aggagcaaag tcacgctaac ctgcctggtc attggcttct acccacctga catccatgtt    1200
gagtggaaga gcaacggaca gccggagcca gagaacacat accgcaccac cccgcccag     1260
caggacgtgg acgggacctt cttcctgtac agcaaactcg cggtggacaa ggcaagatgg    1320
gaccatggag acaaatttga gtgtgcggtg atgcacgagg ctctgcacaa ccactacacc    1380
cagaagtcca tctccaagac tcagggtaaa tgagccaccc gctgcacccc acgtgctctc    1440
gggtcccgcg agctcgcctg agccccagcg ctgtgtacat acgtcccggg ccagcatgaa    1500
ataaa                                                                1505

<210> SEQ ID NO 3
<211> LENGTH: 476
<212> TYPE: PRT
<213> ORGANISM: Sus sp.

<400> SEQUENCE: 3

Met Glu Phe Arg Leu Asn Trp Val Val Leu Phe Ala Leu Leu Gln Gly
  1               5                  10                  15
```

-continued

Val Gln Gly Glu Glu Lys Leu Val Glu Ser Gly Gly Leu Val Gln
          20                  25                  30

Pro Gly Gly Ser Leu Lys Leu Ser Cys Val Gly Ser Gly Phe Thr Phe
              35                  40                  45

Ser Ser Thr Tyr Ile His Trp Val Arg Gln Ala Pro Gly Lys Gly Leu
 50                  55                  60

Glu Trp Leu Ala Gly Leu Tyr Ser Ser Thr Pro Thr Tyr Tyr Ser
 65                  70                  75                  80

Asp Ser Val Lys Gly Arg Phe Asp Ile Ser Arg Glu Asp Ala Gln Asn
                  85                  90                  95

Thr Ala Tyr Leu Gln Met Asn Gly Leu Lys Thr Glu Asp Thr Ala Arg
             100                 105                 110

Tyr Tyr Cys Gly Lys Val Pro Asn Leu Arg Gly Asp Leu Gln Val Leu
             115                 120                 125

Ala Gln Lys Val Ala Arg Thr Leu Pro Trp Gly Pro Gly Val Glu Val
 130                 135                 140

Val Val Ser Ser Ala Pro Lys Thr Ala Pro Ser Val Tyr Pro Leu Ala
145                 150                 155                 160

Pro Cys Gly Arg Asp Val Ser Gly Pro Asn Val Ala Leu Gly Cys Leu
                 165                 170                 175

Ala Ser Ser Tyr Phe Pro Glu Pro Val Thr Val Thr Trp Asn Ser Gly
             180                 185                 190

Ala Leu Thr Ser Gly Val His Thr Phe Pro Ser Val Leu Gln Pro Ser
             195                 200                 205

Gly Leu Tyr Ser Leu Ser Ser Met Val Thr Val Pro Ala Ser Ser Leu
 210                 215                 220

Ser Ser Lys Ser Tyr Thr Cys Asn Val Asn His Pro Ala Thr Thr Thr
225                 230                 235                 240

Lys Val Asp Lys Arg Val Gly Ile His Gln Pro Gln Thr Cys Pro Ile
                 245                 250                 255

Cys Pro Gly Cys Glu Val Ala Gly Pro Ser Val Phe Ile Phe Pro Pro
             260                 265                 270

Lys Pro Lys Asp Thr Leu Met Ile Ser Gln Thr Pro Glu Val Thr Cys
             275                 280                 285

Val Val Val Asp Val Ser Lys Glu His Ala Glu Val Gln Phe Ser Trp
 290                 295                 300

Tyr Val Asp Gly Val Glu Val His Thr Ala Glu Thr Arg Pro Lys Glu
305                 310                 315                 320

Glu Gln Phe Asn Ser Thr Tyr Arg Val Val Ser Val Leu Pro Ile Gln
                 325                 330                 335

His Gln Asp Trp Leu Lys Gly Lys Glu Phe Lys Cys Lys Val Asn Asn
             340                 345                 350

Val Asp Leu Pro Ala Pro Ile Thr Arg Thr Ile Ser Lys Ala Ile Gly
             355                 360                 365

Gln Ser Arg Glu Pro Gln Val Tyr Thr Leu Pro Pro Pro Ala Glu Glu
 370                 375                 380

Leu Ser Arg Ser Lys Val Thr Leu Thr Cys Leu Val Ile Gly Phe Tyr
385                 390                 395                 400

Pro Pro Asp Ile His Val Glu Trp Lys Ser Asn Gly Gln Pro Glu Pro
                 405                 410                 415

Glu Asn Thr Tyr Arg Thr Thr Pro Pro Gln Gln Asp Val Asp Gly Thr
             420                 425                 430

```
Phe Phe Leu Tyr Ser Lys Leu Ala Val Asp Lys Ala Arg Trp Asp His
        435                 440                 445

Gly Asp Lys Phe Glu Cys Ala Val Met His Glu Ala Leu His Asn His
    450                 455                 460

Tyr Thr Gln Lys Ser Ile Ser Lys Thr Gln Gly Lys
465                 470                 475

<210> SEQ ID NO 4
<211> LENGTH: 1523
<212> TYPE: DNA
<213> ORGANISM: Sus sp.

<400> SEQUENCE: 4
atggagtttc ggctgaactg ggtggtcttg tttgctctct tacaaggtgt ccagggtgag      60
gagaagctgg tggagtctgg aggaggcctg gtgcagcctg ggggtctct gaaactctcc     120 tgtgtcggct ctggattcac cttcagtagt acctatattc actgggtccg ccaggctcca    180
gggaagggac tggagtggct ggcaggtctc tacagtagta ctacgccgac ctactactca    240
gactctgtga agggccggtt cgacatctcc agagaggacg cccagaacac ggcctatcta    300
caaatgaacg gcctgaaaac cgaagacacg gcccgctact actgtggaaa ggtaccaaac    360
ctgcgtggtg acctgcaggt acttgctcag aaagttgctc gtactctgcc atggggccca    420
ggcgttgaag tcgtcgtgtc ctcagccccc aagacgcccc atcggtcta ccctctggcc     480 ccctgcggca gggacacgtc tggccctaac gtggccttgg gctgcctggc ctcaagctac    540
ttccccgagc cagtgaccat gacctggaac tcgggcgccc tgaccagtgg cgtgcacacc    600
ttcccatccg tcctgcagcc gtcagggctc tactccctca gcagcatggt gaccgtgccg    660
gccagcagcc tgtccagcaa gagctacacc tgcaatgtca accacccggc caccaccacc    720
aaggtggaca gcgtgttgg aatacaccag ccgcaaacat gtcccatatg cccaggctgt     780
gaagtggccg ggccctcggt cttcatcttc cctccaaaac ccaaggacac cctcatgatc    840
tcccagaccc ccgaggtcac gtgcgtggtg gtggacgtca gcaaggagca cgccgaggtc    900
cagttctcct ggtacgtgga cggggtagag gtgcacacgg ccgagacgag accaaaggag    960
gagcagttca acagcaccta ccgtgtggtc agcgtcctgc ccatccagca ccaggactgg   1020
ctgaagggga aggagttcaa gtgcaaggtc aacaacgtag acctcccagc ccccatcacg   1080
aggaccatct ccaaggctat agggcagagc cgggagccgc aggtgtacac cctgccccca   1140
cccgccgagg agctgtccag gagcaaagtc acgctaacct gcctggtcat ggcttctac    1200 ccacctgaca tccatgttga gtggaagagc aacggacagc cggagccaga gaacacatac   1260
cgcaccaccc cgccccagca ggacgtggac gggaccttct cctgtacag caaactcgcg    1320 gtggacaagg caagatggga ccatggagac aaatttgagt gtcggtgat gcacgaggct    1380 ctgcacaacc actacaccca gaagtccatc tccaagactc agggtaaatg agccaccgc     1440 tgcaccccac gtgctctcgg gtcccgcgag ctcgcctgag cccagcgct gtgtacatac     1500 gtcccgggcc agcatgaaat aaa                                             1523

<210> SEQ ID NO 5
<211> LENGTH: 1089
<212> TYPE: DNA
<213> ORGANISM: Sus sp.

<400> SEQUENCE: 5
gtaccaaacc tgcgtggtga cctgcaggta cttgctcaga aagttgctcg tactctgcca      60
```

```
cgtcacaaac aggaaatcgt agctccagta aaacagaagt tggcccccaa gacggcccca    120
tcggtctacc ctctggcccc ctgcggcagg gacgtgtctg gccctaacgt ggccttgggc    180
tgcctggcct caagctactt ccccgagcca gtgaccgtga cctggaactc gggcgccctg    240
accagtggcg tgcacacctt cccatccgtc ctgcagccgt cagggctcta ctccctcagc    300
agcatggtga ccgtgccggc cagcagcctg tccagcaaga gctacacctg caatgtcaac    360
cacccggcca ccaccaccaa ggtggacaag cgtgttggaa taccagcc gcaaacatgt     420 cccatatgcc caggctgtga agtggccggg ccctcggtct tcatcttccc tccaaaaccc    480
aaggacaccc tcatgatctc ccagaccccc gaggtcacgt gcgtggtggt ggacgtcagc    540
aaggagcacg ccgaggtcca gttctcctgg tacgtggacg gggtagaggt gcacacggcc    600
gagacgagac caaaggagga gcagttcaac agcacctacc gtgtggtcag cgtcctgccc    660
atccagcacc aggactggct gaaggggaag gagttcaagt gcaaggtcaa caacgtagac    720
ctcccagccc ccatcacgag gaccatctcc aaggctatag gcagagccg ggagccgcag     780 gtgtacaccc tgcccccacc cgccgaggag ctgtccagga gcaaagtcac gctaacctgc    840
ctggtcattg gcttctaccc acctgacatc catgttgagt ggaagagcaa cggacagccg    900
gagccagaga acacataccg caccacccg ccccagcagg acgtggacgg gaccttcttc      960
ctgtacagca aactcgcggt ggacaaggca agatgggacc atggagacaa atttgagtgt    1020
gcggtgatgc acgaggctct gcacaaccac tacacccaga gtccatctc caagactcag      1080 ggtaaatga                                                             1089
```

<210> SEQ ID NO 6
<211> LENGTH: 362
<212> TYPE: PRT
<213> ORGANISM: Sus sp.

<400> SEQUENCE: 6

```
Val Pro Asn Leu Arg Gly Asp Leu Gln Val Leu Ala Gln Lys Val Ala
  1               5                  10                  15

Arg Thr Leu Pro Arg His Lys Gln Glu Ile Val Ala Pro Val Lys Gln
             20                  25                  30

Lys Leu Ala Pro Lys Thr Ala Pro Ser Val Tyr Pro Leu Ala Pro Cys
         35                  40                  45

Gly Arg Asp Val Ser Gly Pro Asn Val Ala Leu Gly Cys Leu Ala Ser
     50                  55                  60

Ser Tyr Phe Pro Glu Pro Val Thr Val Thr Trp Asn Ser Gly Ala Leu
 65                  70                  75                  80

Thr Ser Gly Val His Thr Phe Pro Ser Val Leu Gln Pro Ser Gly Leu
                 85                  90                  95

Tyr Ser Leu Ser Ser Met Val Thr Val Pro Ala Ser Ser Leu Ser Ser
            100                 105                 110

Lys Ser Tyr Thr Cys Asn Val Asn His Pro Ala Thr Thr Thr Lys Val
        115                 120                 125

Asp Lys Arg Val Gly Ile His Gln Pro Gln Thr Cys Pro Ile Cys Pro
    130                 135                 140

Gly Cys Glu Val Ala Gly Pro Ser Val Phe Ile Phe Pro Pro Lys Pro
145                 150                 155                 160

Lys Asp Thr Leu Met Ile Ser Gln Thr Pro Glu Val Thr Cys Val Val
                165                 170                 175

Val Asp Val Ser Lys Glu His Ala Glu Val Gln Phe Ser Trp Tyr Val
            180                 185                 190
```

-continued

Asp Gly Val Glu Val His Thr Ala Glu Thr Arg Pro Lys Glu Glu Gln
            195                 200                 205

Phe Asn Ser Thr Tyr Arg Val Val Ser Val Leu Pro Ile Gln His Gln
        210                 215                 220

Asp Trp Leu Lys Gly Lys Glu Phe Lys Cys Lys Val Asn Asn Val Asp
225                 230                 235                 240

Leu Pro Ala Pro Ile Thr Arg Thr Ile Ser Lys Ala Ile Gly Gln Ser
                245                 250                 255

Arg Glu Pro Gln Val Tyr Thr Leu Pro Pro Ala Glu Glu Leu Ser
            260                 265                 270

Arg Ser Lys Val Thr Leu Thr Cys Leu Val Ile Gly Phe Tyr Pro Pro
        275                 280                 285

Asp Ile His Val Glu Trp Lys Ser Asn Gly Gln Pro Glu Pro Glu Asn
    290                 295                 300

Thr Tyr Arg Thr Thr Pro Pro Gln Gln Asp Val Asp Gly Thr Phe Phe
305                 310                 315                 320

Leu Tyr Ser Lys Leu Ala Val Asp Lys Ala Arg Trp Asp His Gly Asp
                325                 330                 335

Lys Phe Glu Cys Ala Val Met His Glu Ala Leu His Asn His Tyr Thr
            340                 345                 350

Gln Lys Ser Ile Ser Lys Thr Gln Gly Lys
        355                 360

<210> SEQ ID NO 7
<211> LENGTH: 217
<212> TYPE: PRT
<213> ORGANISM: Sus sp.

<400> SEQUENCE: 7

Asp Ser Gln Thr Val Ile Gln Lys Pro Ala Ile Ser Phe Ser Leu Gly
1               5                   10                  15

Gly Thr Val Thr Leu Thr Cys Ala Phe Ser Ser Gly Ser Leu Thr Gly
            20                  25                  30

Ile Asn Tyr Pro Ser Trp Phe Gln Arg Thr Pro Gly Gln Pro Pro Gln
        35                  40                  45

Thr Val Ile Tyr Asn Thr Asn Asn Arg Pro Thr Gly Val Pro Ile Arg
    50                  55                  60

Phe Ser Gly Ala Ile Ser Gly Asn Lys Ala Ala Leu Thr Ile Thr Gly
65                  70                  75                  80

Ala Gln Ala Lys Asp Glu Ala Asp Tyr Phe Cys Ala Leu Tyr Lys Ser
                85                  90                  95

Ser Ala Gln Ile Thr Phe Gly Gly Thr His Leu Thr Val Leu Gly
            100                 105                 110

Gln Pro Lys Ala Ala Pro Thr Val Asn Leu Phe Pro Pro Ser Ser Glu
        115                 120                 125

Glu Leu Gly Thr Asn Lys Ala Thr Leu Val Cys Leu Ile Ser Asp Phe
    130                 135                 140

Tyr Pro Gly Ala Val Thr Val Thr Trp Lys Ala Gly Gly Thr Thr Val
145                 150                 155                 160

Thr Gln Gly Val Glu Thr Thr Lys Pro Ser Lys Gln Ser Asn Asn Lys
                165                 170                 175

Tyr Ala Ala Ser Ser Tyr Leu Ala Leu Ser Ala Ser Asp Trp Lys Ser
            180                 185                 190

```
Ser Gly Phe Thr Cys Gln Val Thr His Glu Gly Thr Ile Val Glu
        195                 200                 205

Lys Thr Val Thr Pro Ser Glu Cys Ala
        210                 215

<210> SEQ ID NO 8
<211> LENGTH: 216
<212> TYPE: PRT
<213> ORGANISM: Sus sp.

<400> SEQUENCE: 8

Asp Ser Gln Thr Val Ile Gln Glu Pro Ala Met Ser Val Ser Pro Gly
  1               5                  10                  15

Gly Thr Val Thr Leu Thr Cys Ala Phe Thr Ser Gly Ser Val Thr Thr
                 20                  25                  30

Ser Asn His Pro Gly Trp Tyr Gln Gln Thr Pro Gly Gln Pro Pro Arg
             35                  40                  45

Leu Val Ile Tyr Arg Thr Asn Asn Arg Pro Thr Gly Val Pro Ser Arg
         50                  55                  60

Phe Ser Gly Ala Ile Ser Gly Asn Lys Ala Ala Leu Ser Ile Thr Gly
 65                  70                  75                  80

Ala Gln Ala Asn Asp Glu Ala Asp Tyr Phe Cys Thr Leu Trp Lys Asp
                 85                  90                  95

Asn Thr Tyr Phe Phe Gly Gly Thr Arg Leu Thr Val Leu Gly Gln
            100                 105                 110

Pro Lys Ala Ala Pro Met Val Asn Leu Phe Pro Pro Ser Ser Glu Glu
            115                 120                 125

Leu Gly Thr Asn Lys Ala Thr Leu Val Cys Leu Ile Ser Asp Phe Tyr
130                 135                 140

Pro Gly Ala Val Thr Val Thr Trp Lys Ala Gly Gly Thr Thr Val Thr
145                 150                 155                 160

Gln Gly Val Glu Thr Thr Lys Pro Ser Lys Gln Ser Asn Asn Lys Tyr
                165                 170                 175

Ala Ala Ser Ser Tyr Leu Ala Leu Ser Ala Ser Asp Trp Lys Ser Ser
            180                 185                 190

Ser Gly Phe Thr Cys Gln Val Thr His Glu Gly Thr Ile Val Glu Lys
        195                 200                 205

Thr Val Thr Pro Ser Glu Cys Ala
        210                 215

<210> SEQ ID NO 9
<211> LENGTH: 216
<212> TYPE: PRT
<213> ORGANISM: Sus sp.

<400> SEQUENCE: 9

Asp Ser Gln Thr Val Ile Gln Glu Pro Ala Met Ser Val Ser Pro Gly
  1               5                  10                  15

Gly Thr Val Thr Val Thr Cys Ala Phe Ser Ser Gly Ser Val Thr Ser
                 20                  25                  30

Ser Asp Tyr Pro Ser Trp Phe Gln Gln Thr Pro Gly Gln Pro Pro Arg
             35                  40                  45

Thr Val Ile Tyr Arg Thr Asn Lys Pro Pro Asp Trp Val Pro Gly Leu
         50                  55                  60

Ser Gly Ala Met Ser Gly Asn Lys Ala Ser Leu Thr Ile Thr Gly Ala
 65                  70                  75                  80
```

-continued

```
Gln Ala Glu Asp Glu Ala Asp Tyr Phe Cys Ala Leu Glu Glu Lys Ser
             85                   90                  95

Arg Tyr Gln Val Phe Gly Gly Thr His Leu Thr Val Leu Gly Gln
            100                 105                 110

Pro Lys Ala Ala Pro Thr Val Asn Phe Phe Pro Pro Ser Ser Glu Glu
            115                 120                 125

Leu Gly Thr Asn Lys Ala Thr Leu Val Cys Leu Ile Ser Asp Phe Tyr
    130                 135                 140

Pro Gly Ala Val Thr Val Thr Trp Lys Ala Gly Gly Thr Thr Val Thr
145                 150                 155                 160

Gln Gly Val Glu Thr Thr Lys Pro Ser Lys Gln Ser Asn Asn Arg Tyr
                165                 170                 175

Ala Ala Ser Arg Tyr Leu Ala Leu Ser Ala Ser Asp Trp Lys Phe Ser
            180                 185                 190

Ser Gly Phe Thr Cys Gln Val Thr His Glu Gly Thr Ile Val Glu Lys
        195                 200                 205

Thr Val Thr Pro Ser Glu Cys Ala
    210                 215

<210> SEQ ID NO 10
<211> LENGTH: 216
<212> TYPE: PRT
<213> ORGANISM: Sus sp.

<400> SEQUENCE: 10

Asp Ser Gln Thr Val Ile Gln Glu Pro Ala Met Ser Val Ser Pro Gly
 1               5                  10                  15

Gly Thr Val Ala Leu Thr Cys Ala Phe Ser Ser Gly Ser Val Thr Thr
            20                  25                  30

Ser Asn Tyr Pro Ser Trp Phe Gln Thr Pro Gly Gln Pro Pro Arg Gln
        35                  40                  45

Leu Ile Trp Arg Thr Asn Asn Arg Pro Thr Gly Val Pro Gly Arg Phe
    50                  55                  60

Ser Gly Ala Ile Ser Gly Asn Lys Ala Ala Leu Thr Ile Thr Gly Ala
65                  70                  75                  80

Gln Ala Asn Asp Glu Ala Asp Tyr Phe Cys Thr Leu Cys Lys Ser Thr
            85                  90                  95

Ala Asn Val Ile Phe Gly Gly Thr His Leu Thr Val Leu Gly Gln
            100                 105                 110

Pro Lys Ala Ala Pro Thr Val Asn Leu Phe Pro Pro Ser Ser Glu Glu
            115                 120                 125

Leu Gly Thr Asn Lys Ala Thr Leu Val Cys Leu Ile Ser Asp Phe Tyr
    130                 135                 140

Pro Gly Ala Val Thr Val Thr Trp Lys Ala Gly Gly Thr Thr Val Thr
145                 150                 155                 160

Gln Gly Val Glu Thr Thr Lys Pro Ser Lys Gln Ser Asn Asn Arg Tyr
                165                 170                 175

Ala Ala Ser Arg Tyr Leu Ala Leu Ser Ala Ser Asp Trp Lys Phe Ser
            180                 185                 190

Ser Gly Phe Thr Cys Gln Val Thr His Glu Gly Thr Ile Val Glu Lys
        195                 200                 205

Thr Val Thr Pro Ser Glu Cys Ala
    210                 215
```

<210> SEQ ID NO 11
<211> LENGTH: 805
<212> TYPE: DNA
<213> ORGANISM: Sus sp.

<400> SEQUENCE: 11

| | | | | | |
|---|---|---|---|---|---|
| gtgccaaggt | tgcatgcctg | caggtcgact | agtacggggg | ggggggggggg | gggcaggagg | 60 |
| ctaaagaggc | cccttcccaa | aattgtcccc | accatggcct | gaacggtgct | tctgatcggg | 120 |
| ctcctccctg | tcggctcagg | ggtggattct | caaactgtga | tccaaaaacc | ggcaatctct | 180 |
| ttttctcttg | gagggaccgt | cacactcacc | tgtgccttta | gctctgggtc | actcactggt | 240 |
| attaactacc | ctagctggtt | ccagcggaca | ccaggccagc | ctcctcaaac | tgttatctac | 300 |
| aacacaaaca | accgcccgac | tggggtcccc | attcgcttct | ctggagccat | ctctgggaac | 360 |
| aaagccgccc | tcaccatcac | ggggggccag | gctaaggacg | aggccgacta | cttctgtgct | 420 |
| ctgtataaaa | gtagcgctca | gattacgttc | ggcggtggga | cccatctgac | cgtcctcggt | 480 |
| cagcccaagg | ccgctcccac | ggtcaacctc | ttcccgccct | cctctgagga | gctcggcacc | 540 |
| aacaaggcca | ccctggtgtg | tctaataagt | gacttctacc | cgggcgccgt | gacggtgacc | 600 |
| tggaaggcag | gcggcaccac | cgtcacccag | ggcgtggaga | ccaccaagcc | ctcgaaacag | 660 |
| agcaacaaca | agtacgcggc | cagcagctac | ctggccctgt | ccgccagtga | ctggaaatct | 720 |
| tccagcggct | tcacctgcca | ggtcacccac | gaggggacca | ttgtggagaa | gacagtgacg | 780 |
| ccctccgagt | gcgcctaggg | atccc | | | | 805 |

<210> SEQ ID NO 12
<211> LENGTH: 751
<212> TYPE: DNA
<213> ORGANISM: Sus sp.

<400> SEQUENCE: 12

| | | | | | |
|---|---|---|---|---|---|
| gggggggggc | tgaggaggcc | gcgtcccaag | attgtcccca | ccatggcctg | aacggtgctt | 60 |
| ctgatcgggc | tcctcgctgt | cggctcaggg | gtggattctc | aaactgtgat | ccaggagccg | 120 |
| gcgatgtcag | tgtctcctgg | agggaccgtc | acactcacct | gtgcctttac | atctgggtca | 180 |
| gtcactacta | gtaaccaccc | cggctggtac | cagcagacac | caggccagcc | tccccgactg | 240 |
| gtgatttaca | ggacaaacaa | ccgcccgact | ggggtcccca | gtcgcttctc | tggagccatc | 300 |
| tctgggaaca | aagccgccct | cagcatcacg | ggggcccagg | ctaatgacga | ggccgactat | 360 |
| ttctgtactc | tgtggaaaga | taacacatat | tttttcggcg | gtgggacccg | tctgaccgtc | 420 |
| ctcggtcagc | ccaaggccgc | tcccatggtc | aatctcttcc | cgccctcctc | tgaggagctc | 480 |
| ggcaccaaca | aggccaccct | ggtgtgtcta | ataagtgact | ctacccgggc | gccgtgacg | 540 |
| gtgacctgga | aggcaggcgg | caccaccgtc | acccagggcg | tggagaccac | caagccctcg | 600 |
| aaacagagca | acaacaagta | cgcggccagc | agctacctgg | ccctgtccgc | cagtgactgg | 660 |
| aaatcttcca | gcggcttcac | ctgccaggtc | acccacgagg | ggaccattgt | ggagaagaca | 720 |
| gtgacgccct | ccgagtgcgc | ctagggatcc | c | | | 751 |

<210> SEQ ID NO 13
<211> LENGTH: 657
<212> TYPE: DNA
<213> ORGANISM: Sus sp.

<400> SEQUENCE: 13

| | | | | | |
|---|---|---|---|---|---|
| gtggattctc | agactgtgat | ccaggagccg | gcgatgtcag | tgtctcctgg | agggaccgtc | 60 |

```
acagtcacct gtgcctttag ctctgggtca gtcactagta gtgactaccc aagctggttc      120
cagcagacac caggccagcc tcctcgaact gtcatctaca gaacaaacaa gccgcccgac      180
tgggtcccag gtctctctgg agccatgtct gggaacaaag cgtccctcac catcacgggg      240
gcccaggctg aggacgaggc tgactacttc tgtgctctgg aggaaaagtc acggtatcag      300
gttttcggcg gtgggaccca tttgaccgtc ctcggtcagc ccaaggccgc tcccacggtc      360
aacttcttcc cgccctcctc tgaggagctc ggcaccaaca aggccaccct ggtgtgtcta      420
ataagtgact tctacccggg cgccgtgacg gtgacctgga aggcaggcgg caccaccgtc      480
acccagggcg tggagaccac caagccctcg aaacagagca caacaggta cgcggccagc      540 aggtacctgg ccctgtccgc cagtgactgg aaattctcca gcggcttcac ctgccaggtc      600
acccacgagg ggaccattgt ggagaagaca gtgacgccct ccgagtgcgc ctaggga        657
```

<210> SEQ ID NO 14
<211> LENGTH: 687
<212> TYPE: DNA
<213> ORGANISM: Sus sp.

<400> SEQUENCE: 14

```
cctggactcc tctctcctgt tcgggtggat tctcagactg tgatccagga gccggcgatg      60
tcagtgtctc ctggagggac cgtcgcactc acctgtgcct ttagctctgg gtcagtcact     120
accagtaact accccagctg gttccagaag acaccaggcc agcctccccg acagctgatc     180
tggagaacaa acaaccgccc gactggggtc cccggtcgct ctctggagc catctctggg      240 aacaaagccg ccctcaccat cacgggggcc caggctaatg acgaggccga ctacttttgt     300
actctgtgta aaagtactgc taatgtaatt ttcggcggtg ggacccatct gaccgtcctc     360
ggtcagccca aggccgctcc cacggtcaac ctcttcccgc cctcctctga ggagctcggc     420
accaacaagg ccaccctggt gtgtctaata agtgacttct acccgggcgc cgtgacggtg     480
acctggaaag caggcggcac caccgtcacc cagggcgtgg agacaaccaa gccctcgaaa     540
cagagcaaca caggtacgc ggccagcagg tacctggccc tgtccgccag tgactggaaa      600
ttctccagcg gcttcacctg ccaggtcacc cacgagggga ccattgtgga agacagtg       660 acgccctccg agtgcgccta gggacac                                          687
```

<210> SEQ ID NO 15
<211> LENGTH: 28
<212> TYPE: DNA
<213> ORGANISM: Sus sp.

<400> SEQUENCE: 15

```
gacgctcgag tcatcattta ccctgagt                                          28
```

<210> SEQ ID NO 16
<211> LENGTH: 28
<212> TYPE: DNA
<213> ORGANISM: Sus sp.

<400> SEQUENCE: 16

```
agctaagctt gcccccaaga cggcccca                                          28
```

<210> SEQ ID NO 17
<211> LENGTH: 19
<212> TYPE: DNA
<213> ORGANISM: Sus sp.

```
-continued

<400> SEQUENCE: 17
atgccatatg gtaccaaac                                                19

<210> SEQ ID NO 18
<211> LENGTH: 19
<212> TYPE: DNA
<213> ORGANISM: Sus sp.

<400> SEQUENCE: 18
atgcaagctt caacttctg                                                19

<210> SEQ ID NO 19
<211> LENGTH: 14
<212> TYPE: PRT
<213> ORGANISM: Sus sp.

<400> SEQUENCE: 19

Arg His Lys Gln Glu Ile Val Ala Pro Val Lys Gln Lys Leu
 1               5                  10

<210> SEQ ID NO 20
<211> LENGTH: 42
<212> TYPE: DNA
<213> ORGANISM: Sus sp.

<400> SEQUENCE: 20
cgtcacaaac aggaaatcgt agctccagta aaacagaagt tg                      42

<210> SEQ ID NO 21
<211> LENGTH: 60
<212> TYPE: DNA
<213> ORGANISM: Sus sp.

<400> SEQUENCE: 21
gtaccaaacc tgcgtggtga cctgcaggta cttgctcaga aagttgctcg tactctgcca   60

<210> SEQ ID NO 22
<211> LENGTH: 102
<212> TYPE: DNA
<213> ORGANISM: Sus sp.

<400> SEQUENCE: 22
gtaccaaacc tgcgtggtga cctgcaggta cttgctcaga aagttgctcg tactctgcca   60
cgtcacaaac aggaaatcgt agctccagta aaacagaagt tg                      102
```